US009326660B2

(12) United States Patent
Akimoto et al.

(10) Patent No.: US 9,326,660 B2
(45) Date of Patent: May 3, 2016

(54) ENDOSCOPE SYSTEM WITH INSERTION SUPPORT APPARATUS

(71) Applicant: OLYMPUS CORPORATION, Tokyo (JP)

(72) Inventors: Syunya Akimoto, Kawasaki (JP); Junichi Onishi, Hachioji (JP); Mitsuhiro Ito, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 69 days.

(21) Appl. No.: 14/487,611

(22) Filed: Sep. 16, 2014

(65) Prior Publication Data

US 2015/0057498 A1    Feb. 26, 2015

Related U.S. Application Data

(63) Continuation of application No. PCT/JP2014/055638, filed on Mar. 5, 2014.

(30) Foreign Application Priority Data

Mar. 12, 2013   (JP) .................................. 2013-049290

(51) Int. Cl.
*A61B 1/04*       (2006.01)
*A61B 1/267*      (2006.01)
(Continued)

(52) U.S. Cl.
CPC ........... *A61B 1/00009* (2013.01); *A61B 1/0002* (2013.01); *A61B 1/0005* (2013.01); *A61B 1/00043* (2013.01); *A61B 1/00147* (2013.01);
(Continued)

(58) Field of Classification Search
CPC ............. A61B 1/00009; A61B 1/0002; A61B 1/00043; A61B 1/0005; A61B 1/00147; A61B 1/2676; A61B 5/065
See application file for complete search history.

(56) References Cited

U.S. PATENT DOCUMENTS

2009/0161927 A1* 6/2009 Mori ..................... A61B 6/466
                                                          382/128
2009/0292166 A1* 11/2009 Ito ..................... A61B 1/00009
                                                          600/109

(Continued)

FOREIGN PATENT DOCUMENTS

EP         2 377 457 A1   10/2011
EP         2 581 029 A1    4/2013

(Continued)

*Primary Examiner* — John P Leubecker
(74) *Attorney, Agent, or Firm* — Scully, Scott, Murphy & Presser, P.C.

(57) ABSTRACT

An endoscope system includes: an image storage section that stores image information associated with position information of a luminal organ of a subject; a virtual endoscopic image generating section that generates a virtual endoscopic image endoscopically depicted; an image pickup section that picks up an image in the luminal organ; a position registration processing section that compares the virtual endoscopic image and an endoscopic image, and extracts an virtual endoscopic image similar to the endoscopic image; a position estimation section that estimates a distal end position of an endoscope insertion portion; a feature region determination section that determines whether or not the distal end position exists in a feature region; a storage section that stores information for presentation; and a candidate information presentation control section that presents the virtual endoscopic image based on the information in the storage section, to a display section as candidate information.

12 Claims, 30 Drawing Sheets

(51) Int. Cl.
*A61B 1/00* (2006.01)
*A61B 5/06* (2006.01)
*A61B 6/03* (2006.01)
*A61B 6/00* (2006.01)
*A61B 1/05* (2006.01)

(52) U.S. Cl.
CPC ............ *A61B 1/2676* (2013.01); *A61B 1/05* (2013.01); *A61B 5/065* (2013.01); *A61B 6/032* (2013.01); *A61B 6/5223* (2013.01)

(56) References Cited

U.S. PATENT DOCUMENTS

| | | | | |
|---|---|---|---|---|
| 2009/0292171 A1* | 11/2009 | Ito | ............... | A61B 1/00009 600/111 |
| 2009/0292175 A1* | 11/2009 | Akimoto | ............... | A61B 1/2676 600/156 |
| 2011/0184238 A1* | 7/2011 | Higgins | ............... | A61B 1/00009 600/117 |
| 2011/0234780 A1* | 9/2011 | Ito | ............... | A61B 1/05 348/65 |
| 2011/0282151 A1* | 11/2011 | Trovato | ............... | A61B 5/06 600/117 |
| 2012/0069167 A1* | 3/2012 | Liu | ............... | G06T 7/0026 348/65 |
| 2012/0287238 A1 | 11/2012 | Onishi et al. | | |
| 2012/0289777 A1* | 11/2012 | Chopra | ............... | A61B 1/00009 600/109 |

FOREIGN PATENT DOCUMENTS

| | | |
|---|---|---|
| JP | 2002-200030 A | 7/2002 |
| JP | 2003-265408 A | 9/2003 |
| JP | 2004-089483 A | 3/2004 |
| JP | 2009-056238 A | 3/2009 |
| JP | 2009-279251 A | 12/2009 |
| JP | 2011-000173 A | 1/2011 |
| WO | WO 2011/094518 A2 | 8/2011 |
| WO | WO 2011/102012 A1 | 8/2011 |
| WO | WO 2012/101888 A1 | 8/2012 |

\* cited by examiner

FIG. 9
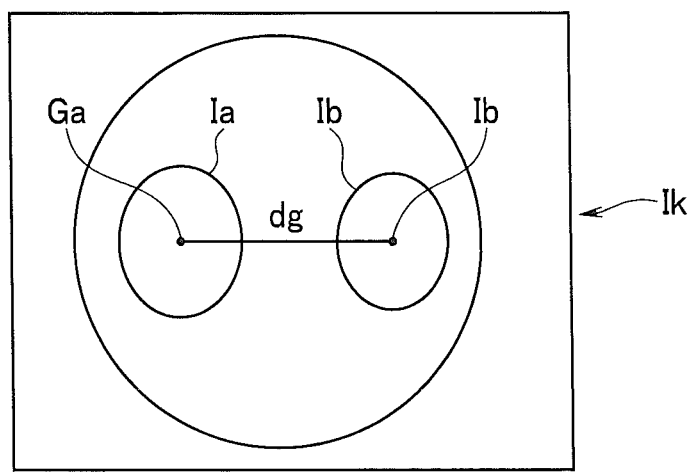
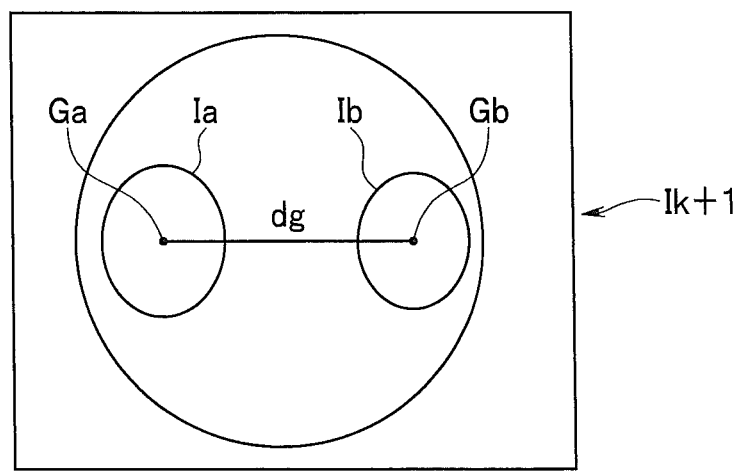

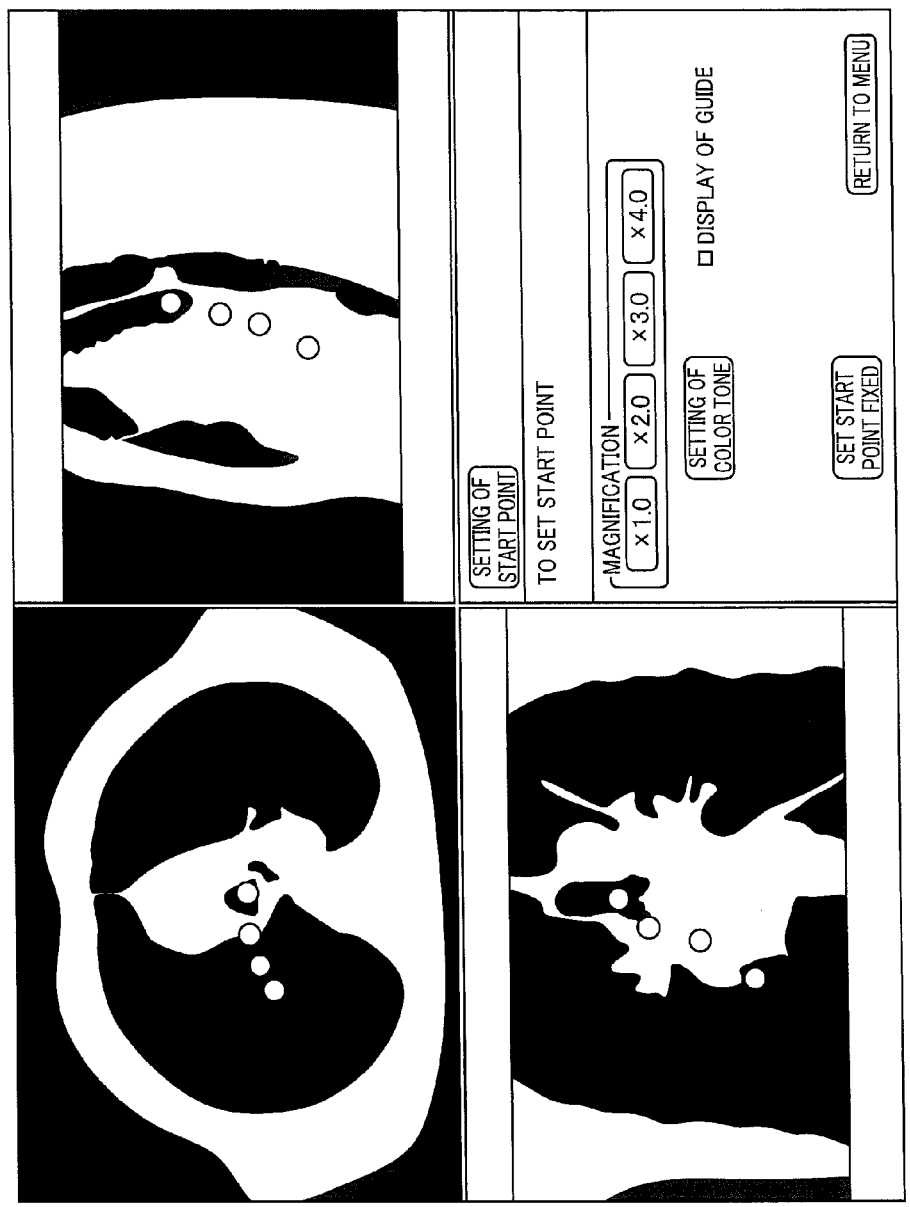

FIG. 12
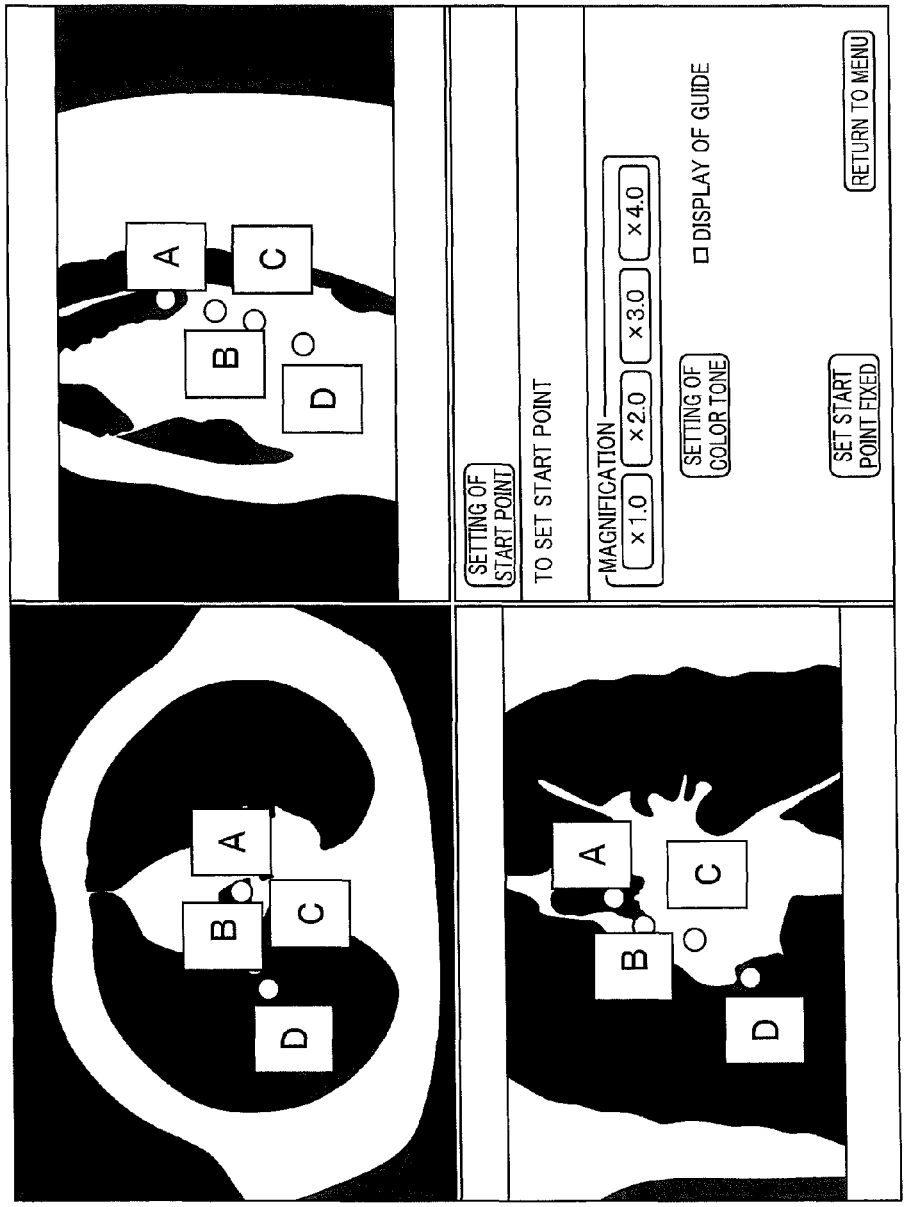
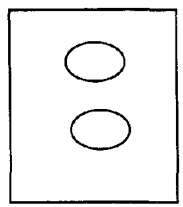
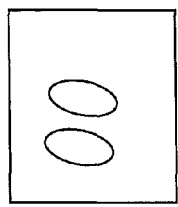
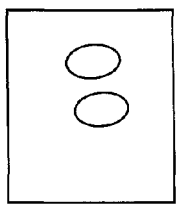
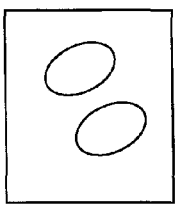

ENDOSCOPE SYSTEM WITH INSERTION SUPPORT APPARATUS

CROSS REFERENCE TO RELATED APPLICATION

This application is a continuation application of PCT/JP2014/055638 filed on Mar. 5, 2014 and claims benefit of Japanese Application No. 2013-049290 filed in Japan on Mar. 12, 2013, the entire contents of which are incorporated herein by this reference.

BACKGROUND OF THE INVENTION

1. Field of the Invention

The present invention relates to an endoscope system that picks up an image in a subject by image pickup means.

2. Description of the Related Art

In recent years, an endoscope having an insertion portion capable of being inserted into a body cavity or the like has been widely used in a medical field and other fields.

Meanwhile, in a case of performing insertion into a luminal organ which is branched complicatedly such as bronchia in a body cavity and examining (an affected tissue of) a target region on a distal end side of a luminal organ, or performing biopsy and treatment by a treatment instrument, there is a case where it is difficult to introduce a distal end of an insertion portion to a vicinity of the target region only by an endoscopic image which is obtained when performing the insertion.

Therefore, there is proposed a system or an apparatus which performs display, etc. for supporting an operation of introducing the distal end of the insertion portion of the endoscope to the vicinity of the target region.

For example, in Japanese Patent Laid-Open Publication No. 2002-200030 as a first conventional example, since it has been difficult to acquire a three-dimensional image by imaging distal bronchia, there is disclosed an apparatus provided with map image synthesizing means that performs registration between a coordinate system of three-dimensional image data of the bronchia and a position of the distal end of the insertion portion, thereafter sequentially stores positions of the distal end of the insertion portion, and synthesizes a locus image on the three-dimensional image data of the bronchia.

Further, in Japanese Patent Laid-Open Publication No. 2004-89483 as a second conventional example, since a diameter of a route to reach a location of an affected part as a target in the bronchia is not known, there is disclosed an apparatus in which, when selecting a bronchia endoscope having an optimal diameter, an insertion route is set in the three-dimensional image of the bronchia, an inner bronchial diameter at a predetermined position in the set insertion route is calculated, and an insertion limit position is calculated from the calculated inner diameter of the bronchia and an insertion diameter of the bronchia endoscope.

Furthermore, in Japanese Patent Laid-Open Publication No. 2009-56238 as a third conventional example, in order to improve precision of image matching between an endoscopic image as an observation image obtained by an endoscope and a virtual endoscopic image generated based on image data in a three-dimensional region of the bronchia, there are disclosed image synthesizing means that displays the virtual endoscopic image, an virtual endoscopic schematic image or the like to be superimposed on the endoscopic image, and image correction means that makes directions of the images coincide with each other.

SUMMARY OF THE INVENTION

An endoscope system according to an aspect of the present invention includes: an image storage section that stores image information associated with position information of a luminal organ of a subject; a virtual endoscopic image generating section that generates a virtual endoscopic image endoscopically depicted from an arbitrary view point position based on the image information; an image pickup section that is provided in an endoscope and picks up an image in the luminal organ of the subject; a position registration processing section that compares the virtual endoscopic image generated by the virtual endoscopic image generating section and an endoscopic image generated by image pickup by the image pickup section, and extracts an virtual endoscopic image similar to the endoscopic image; a position estimation section that estimates a distal end position of an endoscope insertion portion in the luminal organ of the subject based on position information associated with the virtual endoscopic image extracted by the position registration processing section; a feature region determination section that determines whether or not the distal end position of the endoscope insertion portion estimated by the position estimation section exists in a feature region related to a branch in the luminal organ; a storage section that stores, when it is determined that the distal end position of the endoscope insertion portion exists in the feature region by the feature region determination section, at least one of information for presentation including the virtual endoscopic image extracted by the position registration processing section and the position information associated with the virtual endoscopic image; and a candidate information presentation control section that, when the position registration processing section fails to extract a virtual endoscopic image similar to the endoscopic image, presents the virtual endoscopic image corresponding to the distal end position of the endoscope insertion portion which is determined to exist within the feature region by the feature region determination section based on the information stored in the storage section, to a display section as candidate information.

BRIEF DESCRIPTION OF THE DRAWINGS

FIG. 9 is an explanatory diagram of an operation of storing candidate information based on a change in an endoscopic image;

FIG. 11 is a diagram showing an example of displaying estimated positions on tomographic images including bronchia;

FIG. 12 is a diagram showing an example of displaying VBS which corresponds to the position in FIG. 11 to be associated by character information;

DETAILED DESCRIPTION OF THE PREFERRED EMBODIMENTS

Figure 1:
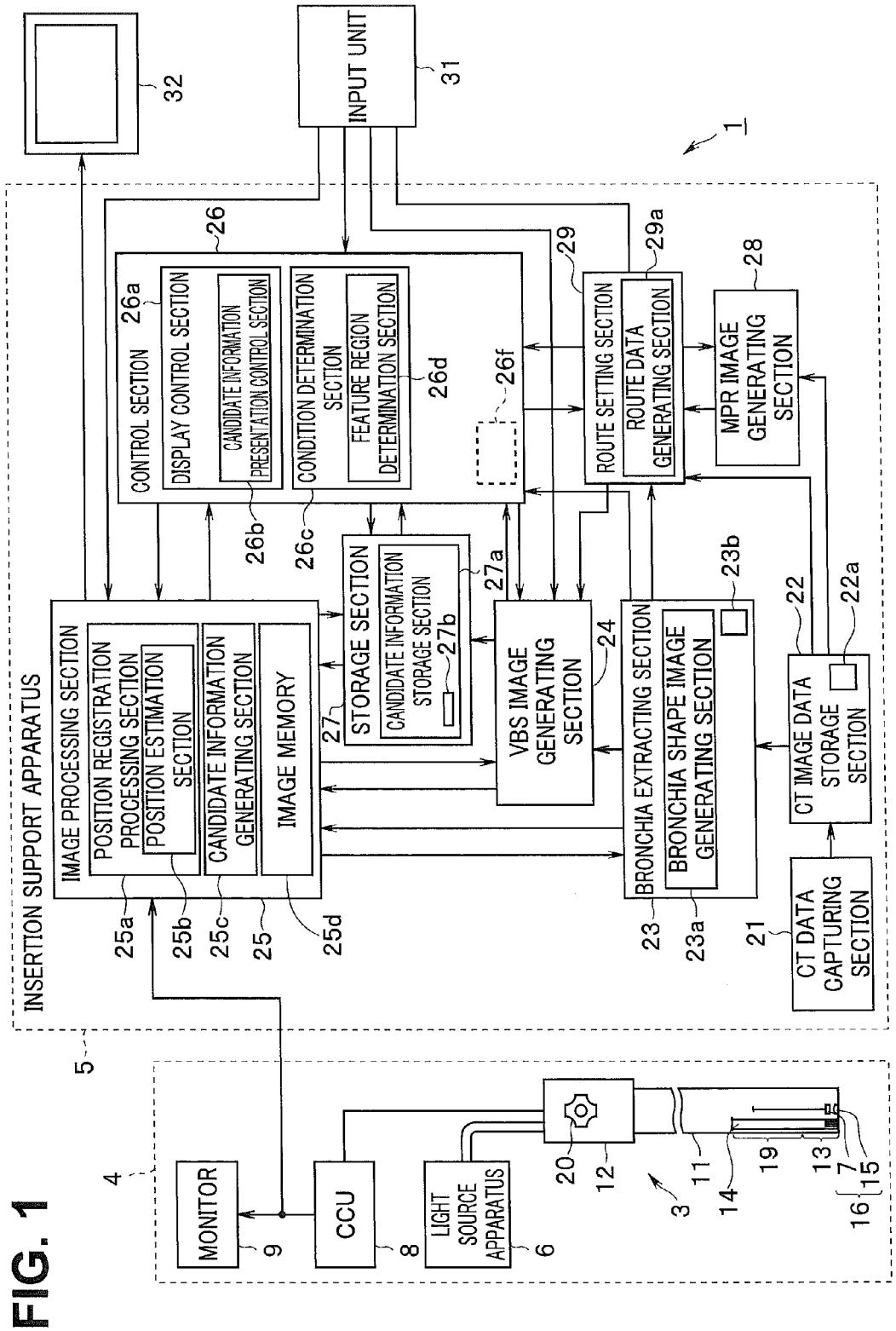
FIG. 1 is a diagram showing an entire configuration of an endoscope system according to a first embodiment of the present invention.

Hereinafter, embodiments of the present invention will be described referring to the drawings.

First Embodiment

As shown in FIG. 1, an endoscope system 1 according to the first embodiment of the present invention is configured to mainly comprise an endoscope apparatus 4 including an endoscope 3 to be inserted into bronchia 2 (FIG. 2A) as a specified luminal organ of a patient as a subject to be examined, and an insertion support apparatus 5 to be used with the endoscope apparatus 4 for performing an insertion support of the endoscope 3.

The endoscope apparatus 4 includes the endoscope 3, a light source apparatus 6 for supplying illumination light to the endoscope 3, a camera control unit (abbreviated as CCU) 8 as a signal processing unit for performing signal processing with respect to an image pickup device 7 which is mounted in the endoscope 3 and constitutes image pickup means, and a monitor 9 for displaying an endoscopic image generated by the CCU 8.

The endoscope 3 is provided with an elongated insertion portion (or endoscope insertion portion) 11 having flexibility and an operation portion 12 provided at a rear end of the insertion portion 11, and an illumination window and an observation window are provided at a distal end portion 13 of the insertion portion 11. A light guide 14 for transmitting the illumination light is inserted through the insertion portion 11 and the operation portion 12, and a light entering end of the light guide 14 is connected to the light source apparatus 6 and the illumination light generated by a light source lamp or an LED, which is not shown, in the light source apparatus 6 is incident on the light entering end. The illumination light transmitted by the light guide 14 is emitted forward from an emitting end (a distal end face) attached to the illumination window.

Further, an objective lens 15 which forms an objective optical system for forming an image of the subject is attached to the observation window and the image pickup device 7 such as a CCD is arranged at an image forming position of the objective lens and an image pickup unit 16 is formed by the objective lens 15 and the image pickup device 7, as image pickup means (or an image pickup section) for picking up an image inside the bronchia 2 as the specified luminal organ into which the insertion portion 11 is inserted.

The image pickup device 7 is connected to the CCU 8 through a signal line inserted through the insertion portion 11 and the operation portion 12.

The CCU 8 generates, by an image signal generating circuit provided therein and not shown, an image signal of a picked-up image corresponding to an optical image formed on an image pickup surface of the image pickup device 7, and outputs the image signal to the monitor 9. The monitor 9 displays an image (a moving image) according to the image signal as the endoscopic image (also referred to as the picked-up image).

It is noted that at the insertion portion 11 of the endoscope 3, a bending portion 19 that is bendable is provided at a rear end of the distal end portion 13 and a surgeon can bend the bending portion 19 in arbitrary directions of up/down and right/left by performing an operation to rotate bending operation knobs 20 provided at the operation portion 12.

The insertion support apparatus 5 includes a CT data capturing section 21 that captures CT data as three-dimensional image information of a patient which has generated by known CT (computed tomography) with respect to the patient who undergoes an examination by the endoscope 3 through a portable storage medium such as a DVD, a Blu-ray Disc and a flash memory, and a CT image data storage section 22 that stores the CT data captured by the CT image data capturing section 21.

Besides, the CT image data storage section 22 may store the CT data (as the three-dimensional image information of the patient as the subject) generated by the CT through a communication line, the internet, etc. The CT image data storage section 22 can be constituted by a hard disc unit, a flash memory, a DVD, or the like.

Further, the CT image data storage section 22, which constitutes image storage means, includes an associated information storage section 22a that stores associated information which associates the CT image data, which is image data separated from the CT data, with three-dimensional position data which is position information separated from the CT data using a first coordinate system to be associated with the CT image data.

Furthermore, the insertion support apparatus 5 includes a bronchia extracting section 23 which comprises a luminal organ extracting circuit, a central processing unit (abbreviated as "CPU"), etc. as luminal organ extracting means, and extracts three-dimensional image data of the bronchia 2 as the specified luminal organ from the CT image data in the CT image data storage section 22.

The bronchia extracting section 23 generates information (shape data) of a three-dimensional shape and image information (image data) of the three-dimensional shape which represent a hollow shape of the bronchia 2 from the extracted three-dimensional image data (more specifically, three-dimensional volume data) of the bronchia 2. That is, the bronchia extracting section 23 includes a bronchia shape image generating section 23a as bronchia shape image generating means that generates a bronchia shape image as an image of the bronchia shape in a hollow three-dimensional shape from the extracted three-dimensional image data of the bronchia 2.

Further, the bronchia extracting section 23, when extracting the three-dimensional data of the bronchia 2, makes extraction of the three-dimensional data to be associated with the three-dimensional position data which corresponds to the three-dimensional data in the first coordinate system (or CT coordinate system). Furthermore, the bronchia extracting section 23 includes an associated information storage section 23b, constituted by a memory and the like, that stores associated information which associates the data of the three-dimensional shape of the bronchia 2 (i.e. bronchia shape data) with the three-dimensional position data.

Further, the insertion support apparatus 5 includes a VBS image generating section 24 as virtual endoscopic image generating means that generates a virtual endoscopic image (which is referred to as "VBS image") as the virtual endoscopic image which corresponds to an endoscopic image generated by image pickup by the image pickup unit 16 provided at the distal end portion 13 of the insertion portion of the endoscope 13.

To the VBS image generating section 24, characteristic information regarding the image pickup unit 16 of the endoscope 3 (a focal length of the objective lens 15, a size and the number of pixels of the image pickup device 7, etc.) is inputted from an input unit 31, for example.

The VBS image generating section 24 is configured to include an image generating circuit, a CPU, etc. that generate a VBS image which virtually depicts an endoscopic image obtained by endoscopically picking up inside of the bronchia 2 with a position of the image pickup unit 16 as a view point, based on information of the position of the image pickup unit 16 (which can be said as a position of the distal end of the insertion portion 11) of the endoscope 3 actually inserted into the bronchia 2, characteristic information of forming an image of the subject in the bronchia 2 by the image pickup unit 16, and the bronchia shape information.

Further, the insertion support apparatus 5 includes an image processing section 25 constituted by a CPU, an image processing circuit, etc., that performs position registration between the endoscopic image inputted from the CCU 8 and the VBS image of the VBS image generating section 24 by image matching, a control section 26 as control means constituted by the CPU, etc., that performs control of the image processing section 25, etc., and a storage section 27 as storage means constituted by a memory, etc., that stores presentation candidate information for performing the insertion support under control of the control section 26.

Further, the insertion support apparatus 5 includes an MPR image generating section 28 that generates a CT tomographic image as a multiplanar reconstruction image (which is referred to as "MPR image") based on the CT image data stored in the CT image data storage section 22, and a route setting section 29 such as a pointing device of a mouse or the like that generates a route setting screen, as a setting screen of an insertion route, which includes MPR images generated by the MPR image generating section 28 for setting a route of the endoscope 3 when inserting the endoscope 3 to a side of a target region inside the bronchia 2.

Figure 2A:
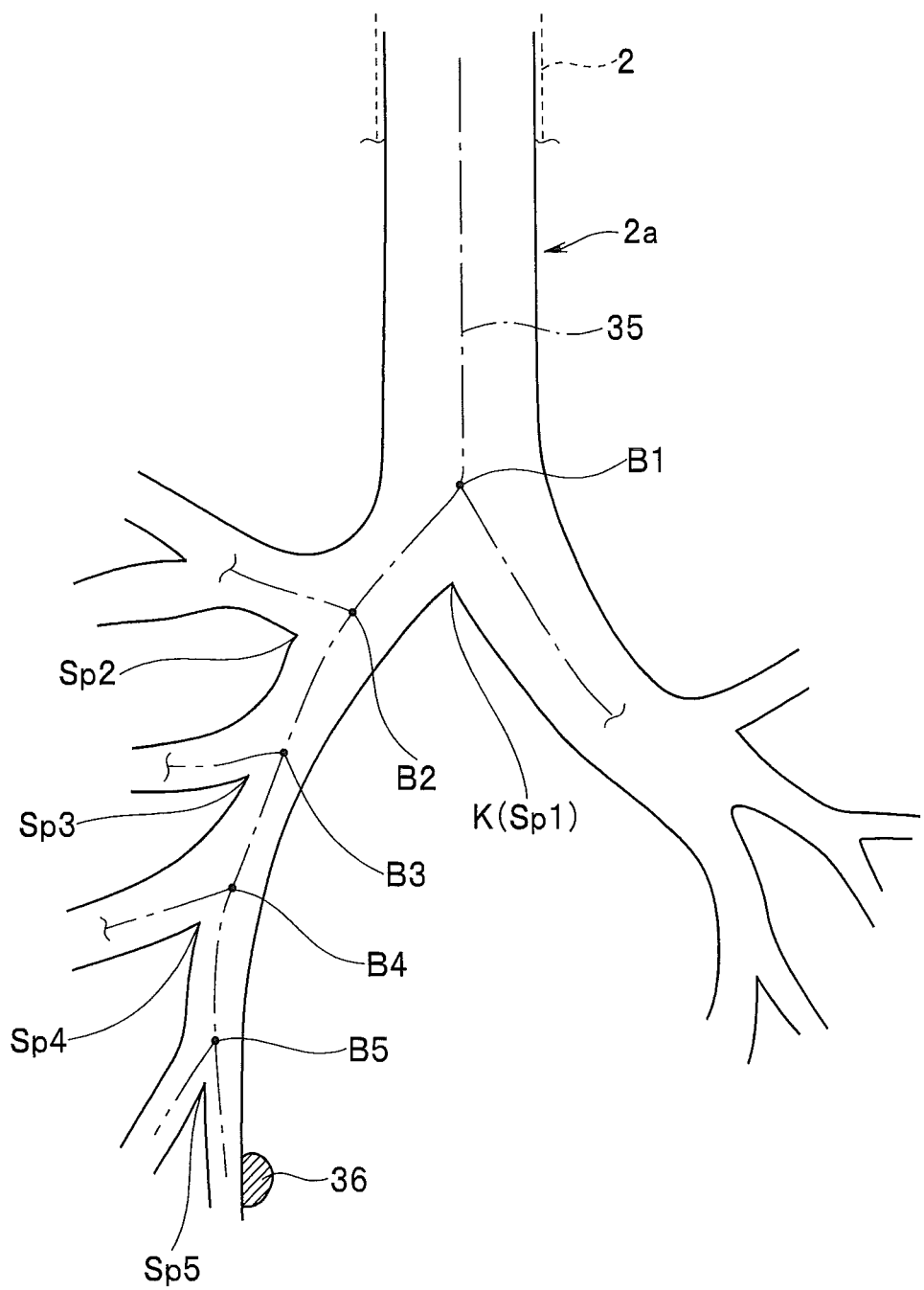
FIG. 2A is a diagram showing a shape image of bronchia.
Figure 10A:
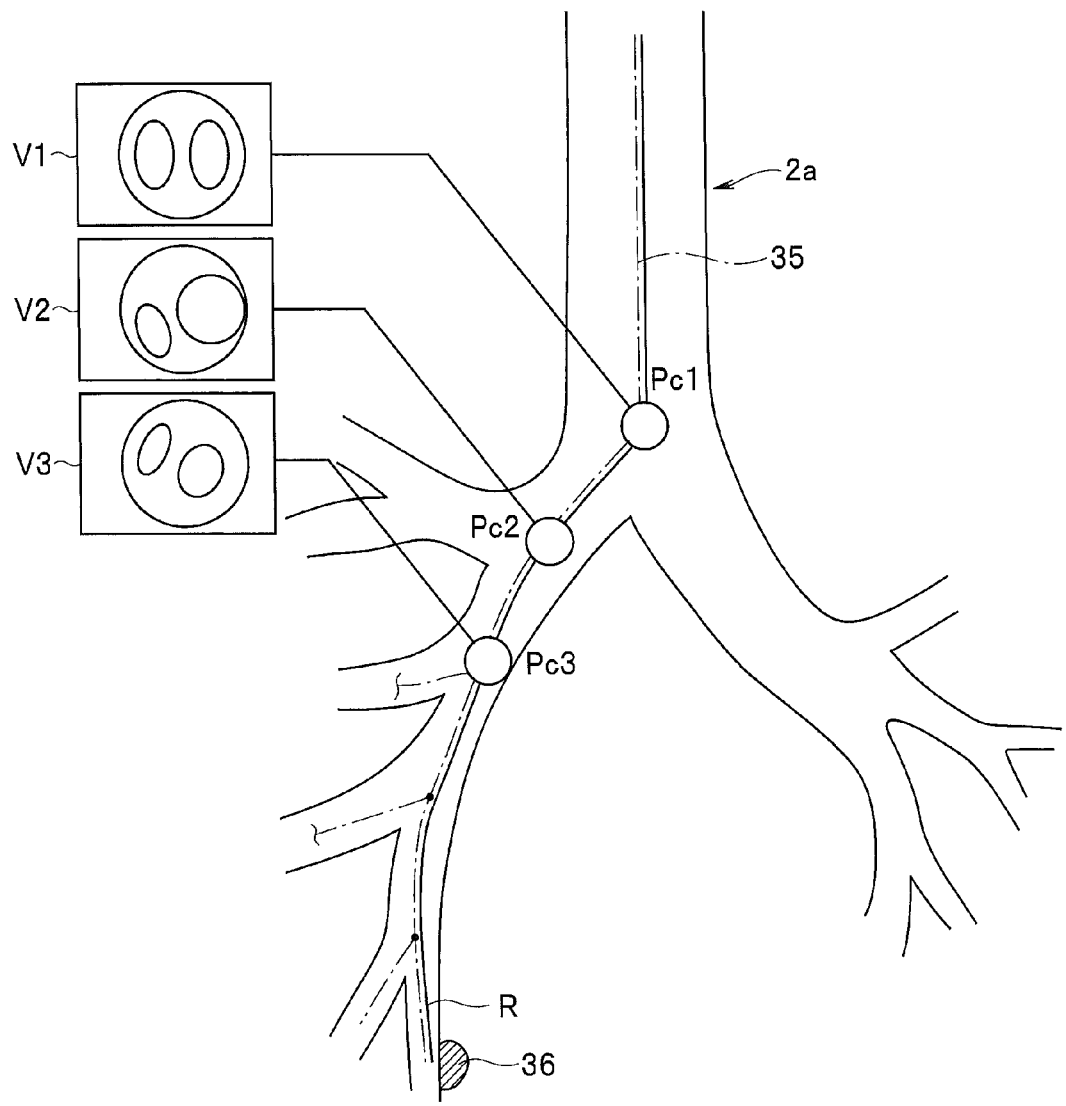
FIG. 10A is a diagram showing a presentation example of candidate information which is different from the presentation example of FIG. 2D.

Then, when a target region 36 is designated from the CT image data as shown in FIG. 2A or FIG. 10A, etc., the route setting section 29 has a function of a route data generating section 29a such as a route data generating circuit or the like that generates a route data from an insertion start position to a target position in the vicinity of the target region 36 in the bronchia 2 from the CT image data and the bronchia shape image 2a. For example, in FIG. 10A, etc., R shows the route to the target position in the vicinity of the target region 36.

Further, the endoscope system 1 includes an input unit 31 constituted by a keyboard and a pointing device and the like for inputting setting information to the route setting section 29. Further, the surgeon is allowed to input parameters or data in performing the image processing from the input unit 31 to the image processing section 25, and to select and instruct a control operation with respect to the control section 26.

Furthermore, when the surgeon performs the route setting, the route setting section 29 sends information of the set route to the VBS image processing section 24, the MPR image generating section 28 and the control section 26. The VBS image processing section 24 and the MPR image generating section 28 respectively generate the VBS image and the MPR image along the path, and the control section 26 performs control of operations of the respective sections along the route.

The endoscopic image generated by the CCU 8 and the VBS image generated by the VBS image processing section 24 are inputted to the image processing section 25. Further, the bronchia shape image generated by the bronchia shape image generating section 23a is also inputted to the image processing section 25.

In the present embodiment, since a sensor for detecting a position of the distal end of the insertion portion 11 is not mounted at the distal end portion 13 of the insertion portion 11 where the image pickup unit 16 is arranged, the three-dimensional position of the distal end of the insertion portion 11 is estimated (or calculated) by the image matching in a position registration processing section 25a by the image processing section 25.

By setting a three-dimensional position (to be a known position) which can be specified in the CT coordinate system from the bronchia shape image 2a such as an entrance or a carina K (see FIG. 2A) of the bronchia 2, or a position in the vicinity of the three-dimensional position as a start point of moving image matching in advance, the VBS image generating section generates the VBS image based on the information of the position.

Then, the surgeon inserts the distal end of the insertion portion 11 so that the endoscopic image looks like the VBS image. By performing such position registration, the position registration processing section 25a of the image processing section 25 starts the image matching such that the endoscopic image and the VBS image match with each other under a set condition (within an error with which predetermined precision is secured). By performing such processing, the position registration processing section 25a includes a function of a position estimation section 25b that detects or calculates the position of the distal end of the insertion portion 11 by estimation.

As described later in a modified example shown in FIG. 5, it may be configured that a position sensor 41 for position detection is provided at the distal end portion 13 and a position estimation section 42b that detects (estimates) the three-dimensional position of the distal end of the insertion portion 11 using the position sensor 14 is provided. Besides, in the present specification, the distal end of the insertion portion 11 is used to have the same meaning of the distal end of the endoscope 3.

Further, the image processing section 25 generates an image to be displayed on the monitor 32 under control of a display control section 26a, which controls display, etc. in the control section 26.

Under control of the display control section 26a, the image processing section 25 usually outputs an image signal (video signal) of the bronchia shape image 2a generated by the bronchia shape image generating section 23a to the monitor 32, and the bronchia shape image 2a is displayed on the monitor 32 as a two-dimensional tomographic image in a cross section cut out along a direction passing a center of a (primary) lumen, for example, as shown in FIG. 2A. Besides, it is not limited to the case of being displayed as the two-dimensional tomographic image, but the image may be displayed as a three-dimensional image. In the case of being displayed as the three-dimensional image, the image may be displayed as a projected drawing according to parallel projection, or as a perspective drawing so that the inside of the lumen can be seen, for example.

Further, as shown in FIG. 2A, a core line 35 passing the center of the lumen of the bronchia 2 is also displayed in the bronchia shape image 2a displayed on the monitor 32. Besides, the core line 35 is generated by the bronchia shape image generating section 23a, for example, but may be created in the image processing section 25.

Since the core line 35 is displayed when the user such as the surgeon inserts the insertion portion 11 from the distal end thereof into the bronchia 2, the user can easily perform an operation of insertion by referring to the display. Further, by performing the operation of insertion along the core line 35, the estimation of the position of the distal end of the insertion portion 11 by the image matching can be performed in a short time.

The image processing section 25 performs processing of estimating a position to which the distal end of the insertion portion 11 has moved or a distance of the movement using matching of the images (image matching) between the endoscopic image and the VBS image in the operation of insertion into a deeper side (distal end side) of the bronchia 2.

That is, in the case where the images match with each other at a certain location, since the image pickup unit 16 moves with an operation of moving the distal end of the insertion portion 11 along the core line 35 (for insertion), the endoscopic image changes.

In this case, the position registration processing section 25a selects a VBS image which best matches with the endoscopic image using the VBS images (outputted from the VBS image processing section 24) during the movement on the route along the core line 35 by image processing, and the three-dimensional position corresponding to the selected VBS image is calculated (estimated) as the position of the distal end of the insertion portion 11. Therefore, the distance of the movement can be also calculated (estimated) from a difference between the two portions.

Besides, since there is a case where the distal end of the insertion portion 1 is moved at a position deviated from the core line 35, it may be configured such that the VBS image processing section 24 generates VBS images at positions which are eccentric from the core line 35 by an appropriate distance and the generated VBS images are outputted to the position registration processing section 25a. With this configuration, a range of position estimation by image matching can be extended. It may be configured that the control section 26 corrects the route data generated by the route data generating section 29a (before the insertion of the insertion portion 11 of the endoscope 3) by the position of the distal end of the insertion portion 11 calculated by the position registration processing section 25a.

Further, the control section 26 has a function of a condition determination section 26c, constituted by a comparison circuit, etc. that performs determination of whether or not the distal end of the insertion portion 11 estimated by the image processing section 25 meets a predetermined condition, and stores the position of the distal end of the insertion portion 11 in the storage section 27 when it is determined that the predetermined condition is met. In this case, the VBS image corresponding to the position of the distal end of the insertion portion 11 is stored with the position of the distal end in the storage section 27 as candidate information (for presentation) to be presented as necessary.

In other words, the storage section 27 stores the estimated (calculated) position of the distal end of the insertion portion 11 when it is determined that the predetermined condition is met as candidate portion information to be presented later, and has a function of a candidate information storage section 27a as storage means that stores the candidate position information and the VBS image corresponding to the candidate position information as the candidate information for presentation. In this case, the candidate information for presentation is constituted by the information of a candidate position (candidate portion information) and the VBS image corresponding to the information of the candidate position. The VBS image corresponding to the information of the candidate position (i.e. generated at the candidate position) may be referred to as a candidate VBS image.

Besides, as the candidate information (for presentation) to be stored in the candidate information storage section 27a, the endoscopic image corresponding to the information of the candidate position (i.e. generated at the candidate position) may be also stored with the VBS image corresponding to the information of the candidate position. The endoscopic image in this case may be referred to as a candidate endoscopic image in the same manner as the candidate VBS image.

Further, the image processing section 25 has a function of a candidate information generating section 25c that generates candidate information to be displayed on the monitor 32 as candidate information under control to present the candidate information by a candidate information presentation control section 26b of the display control section 26a. Further, the image processing section 25 includes an image memory 25d that temporally stores the endoscopic image and the VBS image and is used as a work area for the image processing when performing the image matching between the endoscopic image and the VBS image. Besides, the image memory 25d may be provided outside of the image processing section 25.

The condition determination section 26c has a function of a feature region determination section 26d that performs determination as to whether or not the distal end of the insertion portion 11 is located in a feature region as a characteristic region which relates to a branch in the bronchia 2, as the predetermined condition. Further, as described later, when it is determined that the distal end of the insertion portion 11 is located (or exists) in the feature region by the feature region determination section 26d, the candidate information is stored in the candidate information storage section 27a.

Figure 2B:
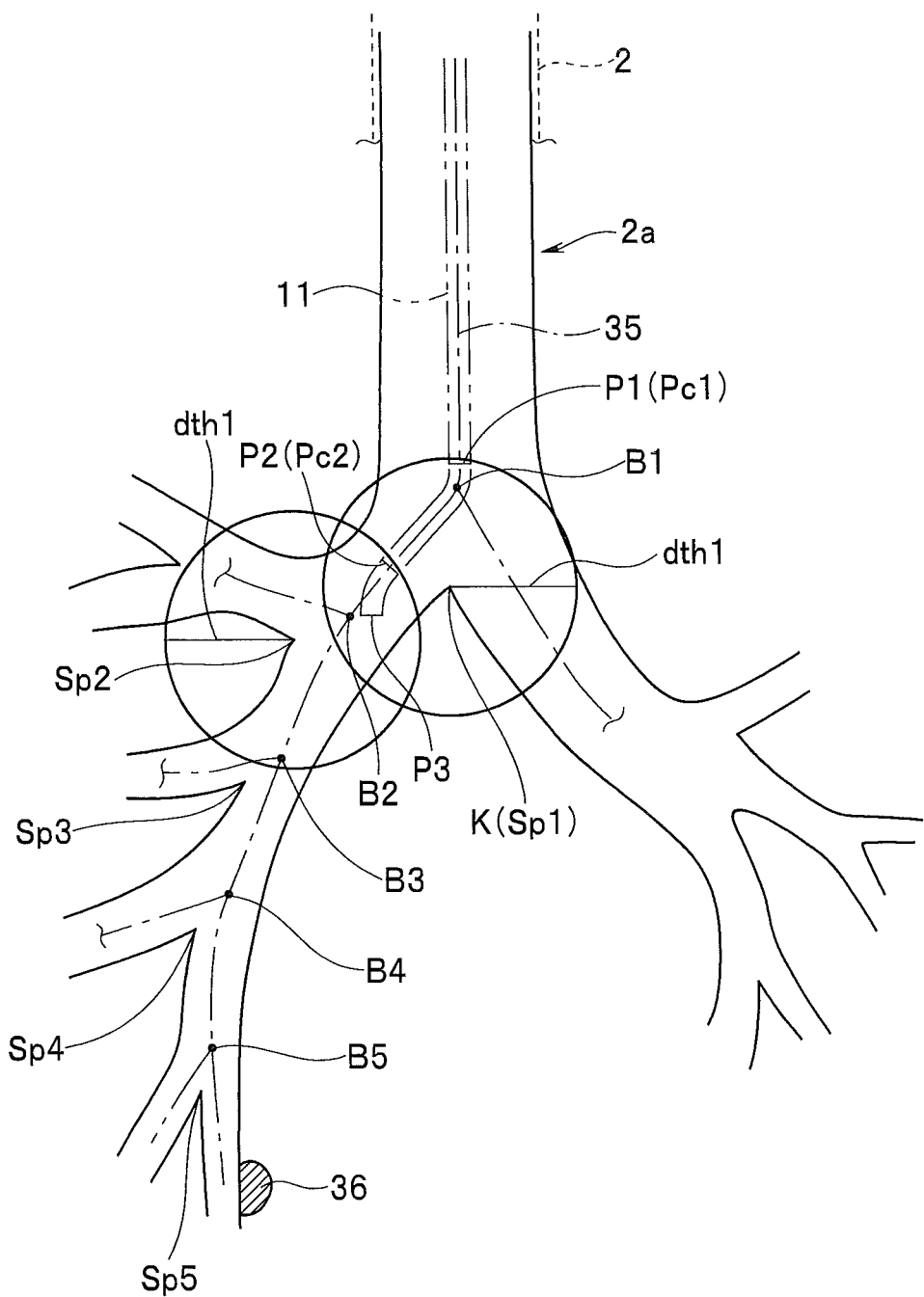
FIG. 2B is a diagram showing a distance range of a fixed value from a spur in the shape image of the bronchia.
Figure 2C:
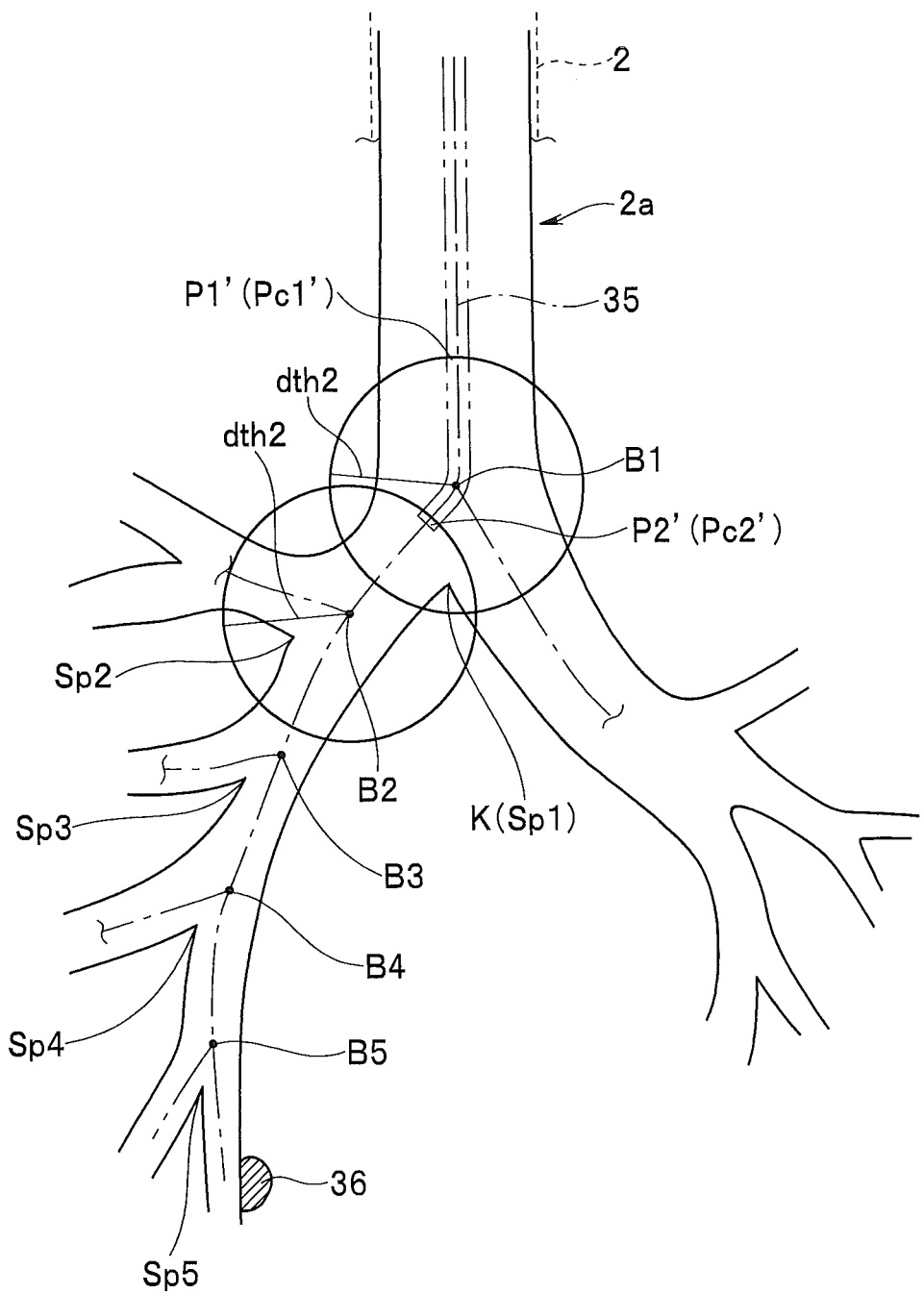
FIG. 2C is a diagram showing a distance range of a fixed value from a branch point in the shape image of the bronchia.

In the present embodiment, a fixed value dth is set with respect to a distance between two positions (or points), as the above predetermined condition. Then, it is set such that the distal end of the insertion portion 11 is determined to be located in the feature region that meets the predetermined condition and the candidate information is stored in the storage section 27 when a distance between the position of the distal end of the insertion portion 11 and a position of a spur Spi of bifurcation such as a carina K as shown in FIG. 2B and FIG. 2C or a distance between the position of the distal end of the insertion portion 11 and a branch point Bi at which the core line 35 is branched as shown in FIG. 2B and FIG. 2C is within the fixed value dth such as dth1, dth2.

Besides, the setting of the feature region and the fixed value dth can be designated by the surgeon from the input unit 31, for example. As described, in the present embodiment, in the process of inserting the insertion portion 11 into bronchia 2, by storing the candidate information prior to the present position of the distal end of the insertion portion 11 in the storage section 27, it is configured that, when it is necessary to perform the position registration again (i.e. re-registration of position) because of lowering of precision of the position estimation of the distal end of the insertion portion 11 (using the image matching) by the movement operation of the insertion portion 11 after the initial position registration by the image matching, the candidate information for the re-registration of position can be presented.

Further, the surgeon may input an instruction to perform the re-registration of position to the image processing section 25 or the control section 26 through the keyboard, the mouse or the like which constitutes the input unit 31.

When the instruction of the re-registration of position or the like is made (or a trigger input is made), the display control section 26a of the control section 26 reads the candidate information in the vicinity of the present position of the distal end of the insertion portion 11 from the candidate information storage section 27a of the storage section 27 and performs control of presenting the candidate information on the monitor 32 through the image processing section 25.

The display control section 26a which performs the control of presenting the candidate information on the monitor 32 has a function of the candidate information presentation control section 26b that performs control of the candidate information presentation. Besides, it may be configured such that the display control section 26a reads the candidate information (for presentation) from the candidate information storage section 27a and performs the control of presenting the candidate information on the monitor without the image processing section 25 interposed. In presenting the candidate information on the monitor 32, the information of the candidate position as a candidate when performing an image comparison and the VBS image corresponding to the information of the candidate position are displayed on the bronchia shape image 2a shown in FIG. 2D as the two-dimensional tomographic image, for example.

As described above, the position registration processing section 25a of the image processing section 25 estimates (calculates) the distal end of the insertion portion 11 using the image matching when the distal end of the insertion portion 11 is moved, but there is a case where an image matching error occurs in which the image matching cannot be performed within set precision.

In this case, the position registration processing section 25a of the image processing section 25 issues a signal of an image matching error to display an occurrence of the image matching error on the monitor 32. Further, the position registration processing section 25a sends the signal of the image matching error to the control section 26, and the candidate information presentation control section 26b of the control section 26 performs control of presenting the candidate information on the monitor 32.

Thus, the monitor 32 constitutes candidate information presenting means that presents the candidate information to the surgeon. Besides, the candidate information presenting means may be defined to include the candidate information storage section 27a that stores the candidate information (for presentation), and the image processing section 25 and the candidate information presentation control section 26b for outputting the image signal of the candidate information.

The surgeon performs the position registration processing again using the candidate information. By performing the re-registration processing of position, the surgeon is enabled to continue the insertion operation of the insertion portion 11 from the vicinity of the position where the re-registration processing of position is performed.

Further, when the surgeon judges that the precision of the image matching is lowered, the surgeon may give an instruction of the re-registration of position so as to perform the above processing. Besides, the position registration processing section 25a, the candidate information generating section 25c, the bronchia extracting section 23, the VBS image processing section 24 and the control section 26 may be configured using the CPU, or may be configured using an apparatus provided as hardware such as a FPGA (Field Programmable Gate Array), or a dedicated electrical circuit device.

The endoscope system 1 having the above configuration includes features of: the CT image data storage section 22 as the image storage means that stores three-dimensional image information of a subject which is acquired in advance, the VBS image processing section 24 as the virtual endoscopic image generating means that generates the virtual endoscopic image endoscopically depicted with respect to the three-dimensional image information from a predetermined view point position, the image pickup unit 16 that is provided in the endoscope 3 as the image pickup means for picking up an image inside the specified luminal organ, the position estimation section 25b as the position detecting means that detects the position of the distal end of the endoscope insertion portion 11 in the specified luminal organ of the subject, the monitor 32 as the candidate information presenting means that presents the candidate position information when performing image comparison between the virtual endoscopic image and the endoscopic image generated by the image pickup by the image pickup means and the virtual endoscopic image corresponding to the candidate position information as the candidate information on the two-dimensional tomographic image which is obtained by cutting the three-dimensional image information in the predetermined direction based on the position information of the distal end of the endoscope insertion portion 11 by the position detecting means.

Figure 3:
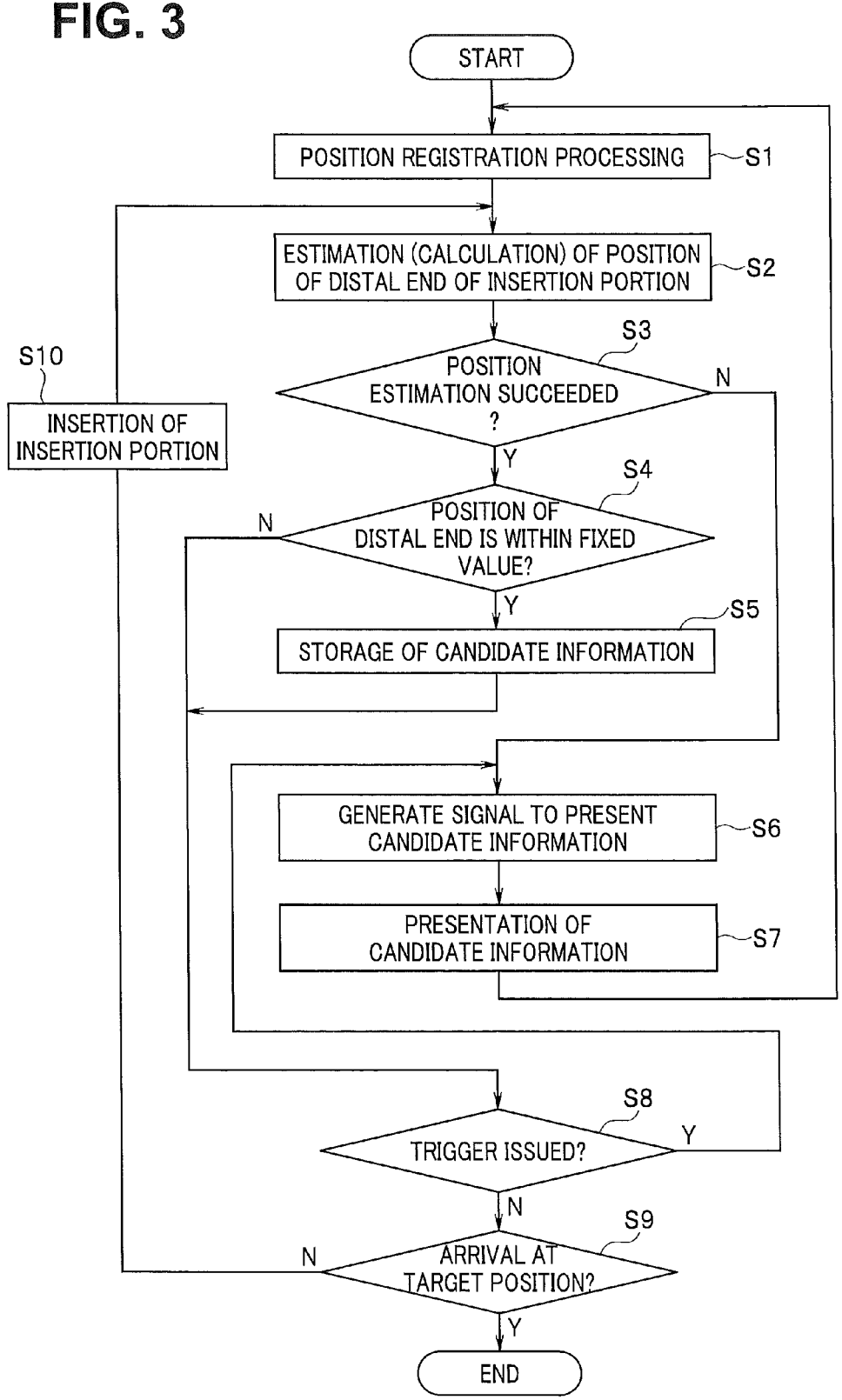
FIG. 3 is a flowchart showing a typical example of processing contents in the first embodiment.

Next, typical processing in the present embodiment will be described referring to a flowchart of FIG. 3. When power supply of the endoscope apparatus 4 and the insertion support apparatus 5 of the endoscope system 1 are turned on and respective components are in operating states, at least one region, which is easy for the surgeon to determine the position of the distal end of the insertion portion 11 of the endoscope 3 in the endoscopic image, such as a position of the entry of the bronchia 2 of the patient is set to a reference position in first Step S1 as shown in FIG. 3.

Then, the position registration processing section 25a of the image processing section 25 outputs (an image signal of) a VBS image at the reference position of the VBS image processing section 24 to the monitor 32. The surgeon designates one of the reference positions through the input unit 31, inserts the distal end of the insertion potion 11 to the designated reference position and instructs the position registration processing section 25a of the image processing section 25 to perform the position registration processing.

After performing the position registration processing of Step S1, the position registration processing section 25a estimates (calculates) the position of the insertion portion 11 by the image matching on the bases of the result of the position registration processing, as shown in Step S2. Specifically, the VBS image which matches with the endoscopic image best is calculated by the image processing using the information of the position registration processing as an initial value of the image matching.

In Step S3, the position registration processing section 25a determines whether or not the estimation of the distal end of the insertion portion 11 by the image matching has been performed within a predetermined condition (e.g. whether or not the estimated position is located inside the bronchia) (that is, whether or not the estimation of the position has succeeded). If a determination result in Step S3 is success, the position of the distal end of the insertion portion 11 which is estimated by the position registration processing section 25a of the image processing section 25 is displayed to be superimposed on the bronchia shape image 2a at the estimated position on the monitor 32, and the processing of Step S4 is performed. On the other hand, if the determination result is failure, the processing of Step S6 is performed.

The position information of the distal end of the insertion portion 11 estimated by the position registration processing section 25a in Step S4 is inputted to the feature region determination section 26d of the control section 26. Then, the feature region determination section 26d determines whether or not the estimated position of the distal end of the insertion portion 11 is located in the feature region within the fixed value dth (such as dth1, dth 2) from the spur Spi or the branch point Bi of the bronchia 2. If a determination result of Step S4 is location within the fixed value dth, the candidate information is stored in the storage section 27 as shown in Step S5.

For example, when it is determined that a distal end P1 of the insertion portion 11 is within the fixed value dth1 (=dth) from the carina K (a first spur Sp1) as shown in FIG. 2B, an estimated position P1 of the distal end of the insertion portion 11 is set to be a candidate portion Pc1, and (information of) the candidate position Pc1 and also a corresponding VBS image I1 are stored in the storage section 27 as the candidate information.

Further, when the distal end of the insertion portion 11 is inserted into a deeper side of the carina K and a distal end P2 of the insertion portion 11 is located within the fixed value dth1 from the next spur Sp2, an estimated position P2 of the distal end of the insertion portion 11 is set to be a candidate position Pc2, and (information of) the candidate position Pc2 and also a corresponding VBS image I2 are stored in the storage section 27 as the candidate information. After the processing of Step S5, the procedure proceeds to the processing of Step S8.

On the other hand, if the distal end of the insertion portion 11 has not reached location within the fixed value dth1 from the spur Sp1 in Step S4, the processing of Step S8 is executed without performing the processing of recording the candidate information of Step S5. Besides, FIG. 2B shows the example of storing the candidate position Pc1 when it is determined that the distal end of the insertion portion 11 has reached the location within the fixed value dth1 from the spur Sp1, but it may be configured that the candidate position Pc1' is stored when it is determined that the distal end of the insertion portion 11 is located within the fixed value dth2 (=dth) from the branch point Bi. It is noted that FIG. 2C shows that the case where the distal ends P1' and P2' are located within the fixed value dth 2 from the branch points B1 and bB2, respectively. Further, the fixed value dth1 and the fixed value dth2 may be set to be the same value or set to be different values.

In Step S8, it is detected whether or not the surgeon issues an instruction signal (a trigger) to present the candidate information from the input unit 31. This detection is performed for a case where the surgeon judges to perform the position registration again and issues the instruction signal in a case where it cannot be detected that the estimation by the image matching fails, for example, in a case where the estimated position by the image matching meets the predetermined condition (that the estimated position is located inside the bronchia) but the estimated position shows clearly a different position, e.g. when the endoscope is moved rapidly.

If there is no trigger in Step S8, the position registration processing section 25a performs determination (estimation) of whether or not the distal end of the insertion portion 11 has been inserted to a target position in the next Step S9.

If the distal end of the insertion portion 11 has not been inserted to the target position, the surgeon inserts the distal end of the insertion portion 11 into the deeper side of the bronchia 2 referring to the display displayed on the monitor 32, as shown in Step S10. After the process of Step S10, the procedure returns to Step S2 in which the estimation of the distal end position of the insertion portion 11 is performed using the estimated position by the previous image matching in place of the information of the position registration as an initial value of the image mage matching. On the other hand, when the insertion is performed to the target position in Step S 19, the operation of insertion of FIG. 3 is terminated.

In contrast, if the position estimation does not succeed but fails in Step S3, or if a trigger has been issued in Step S8, indication of a stop of the processing, such as matching error, is displayed on the monitor 32. In this case, the display control section 26a automatically issues an instruction signal to present the candidate information, as shown in Step S6.

Then, the candidate information is read from the candidate information storage section 27a of the storage section 27. Then, the candidate information is displayed on the monitor 32 as shown in Step S7. For example, if the matching error occurs at a position P3 of the distal end of the insertion portion 11 after entering the region within the fixed value dth1 from the spur Sp2 in FIG. 2B, a candidate position (a candidate position Pc2 in this case) which is stored last in (the candidate information storage section 27a of) the storage section 27 before the occurrence of the matching error and the VBS image corresponding to the candidate position Pc2 are presented as the candidate information.

Figure 2D:
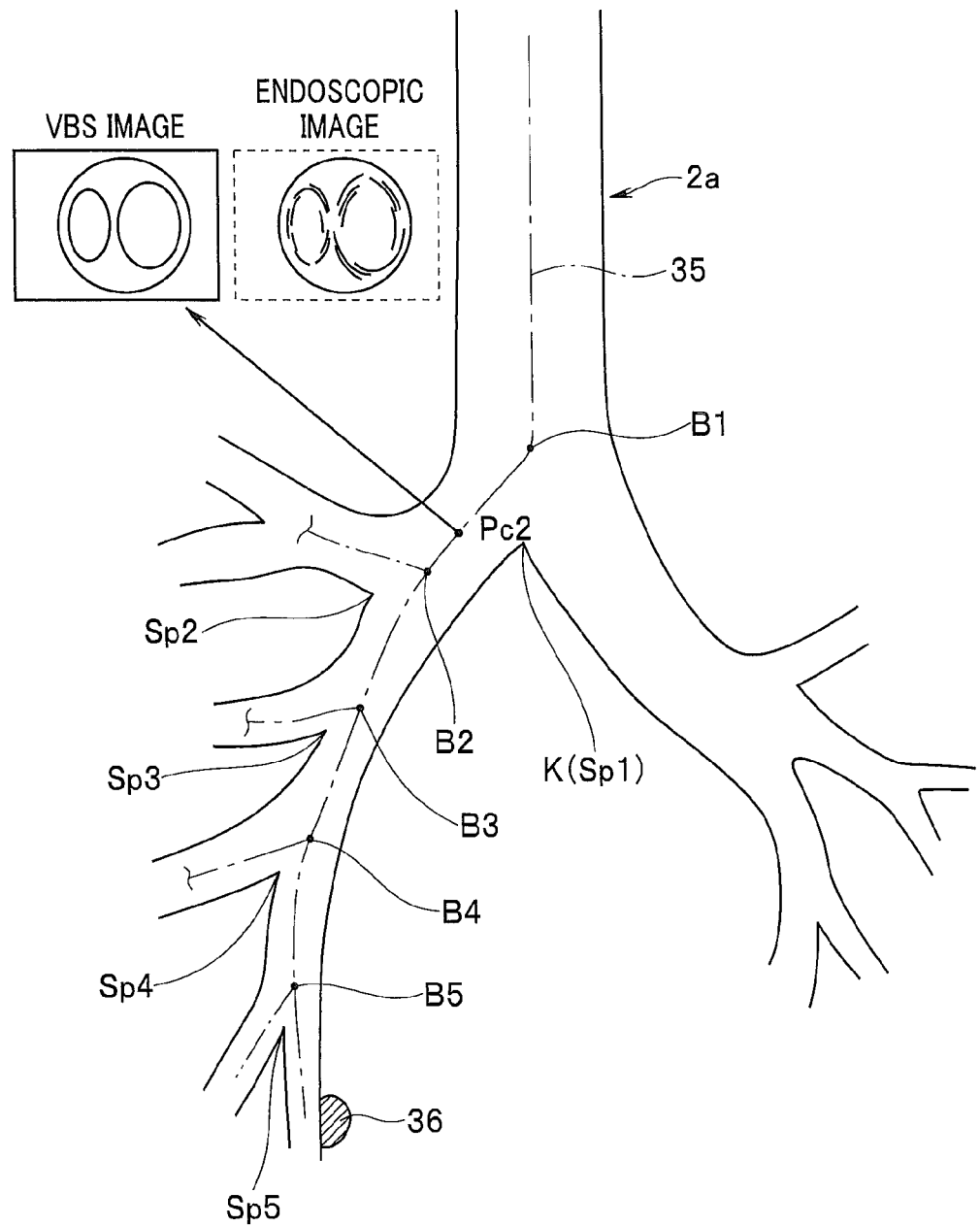
FIG. 2D is a diagram showing a presentation example of candidate information.

A presentation example in this case is shown in FIG. 2D. As shown in FIG. 2D, the candidate position Pc2 and also the VBS image corresponding to the candidate position Pc2 are displayed on the bronchia shape image 2a as the candidate information. Besides, in presenting the candidate information, it may be configured such that the endoscopic image corresponding to the candidate position Pc2 is displayed as shown by the dotted line, as mentioned above.

Further, in this case, the endoscopic image may be displayed at a position in the vicinity of the VBS image with the same display magnification so as to be easily compared.

Furthermore, it may be configured that one of the VBS image and the endoscopic image is displayed movably so that the user can perform superimposed display (synthesis display) of one of the images on the other of the images by a mouse or the like. With this configuration, the user is allowed to confirm a degree of image matching easily. Further, FIG. 2D shows the presentation example of one piece of the candidate information. However, a plurality of pieces of the candidate information may be presented as shown in FIGS. 10A-10F which will be described later.

When the candidate information is displayed, the procedure returns to Step S1 in which the surgeon performs the process of the position registration again referring to the candidate information displayed on the monitor 32.

According to the present embodiment which operates as described above, it is configured that the candidate information for presentation is stored in the storage section 27 in the middle of performing the operation of inserting the insertion portion 11 and in the case such as the case where the estimation of the position of the distal end of the insertion portion 11 results in failure, the candidate information for presentation which is suitable for the position registration can be presented, and therefore the operation of insertion can be performed smoothly.

Further, in the present embodiment, since the position estimation of the distal end of the insertion portion 11 is performed using the image processing of the image matching, an error tends to become larger from a state of the initial position registration due to an algorithm of the image processing. In such a case, it is made possible to perform the operation of insertion into the deeper side with the error reduced by the re-registration of position by re-matching of image from the vicinity of the position at which the re-registration of position is performed.

The condition in the above described may be modified in the following manner.

(a) There has been described the example in which the candidate information (for presentation) is stored in the storage section 27 when the estimated position of the distal end of the insertion portion 11 meets one condition of location within the fixed value dth1 or dth2. However, it is not limited to this condition.

(b) The candidate information may be stored when two conditions that the position of the distal end of the insertion portion 11 is within the fixed value dth1 from the spur Sp1 and within the fixed value dth2 from the branch point Bi are met.

(c) Further, the candidate information may be stored further when a distance between the estimated position of the distal end of the insertion portion 11 and the core line 35 is within a fixed value dth3 in the conditions (a) or (b).

(d) Furthermore, the candidate information may be stored when an image of a branch appears in the endoscopic image in any of the conditions (a), (b) and (c).

(e) Further, the fixed values dth1-dth3 may be set to be the same value and to be values in accordance with a bronchial diameter at the spur SPi or the branch point Bi, or in accordance with a distance to a branch region at which a bronchial tube branches or a distance from the carina to the branch, in any of the conditions (a), (b), (c) and (d).

Figure 4:
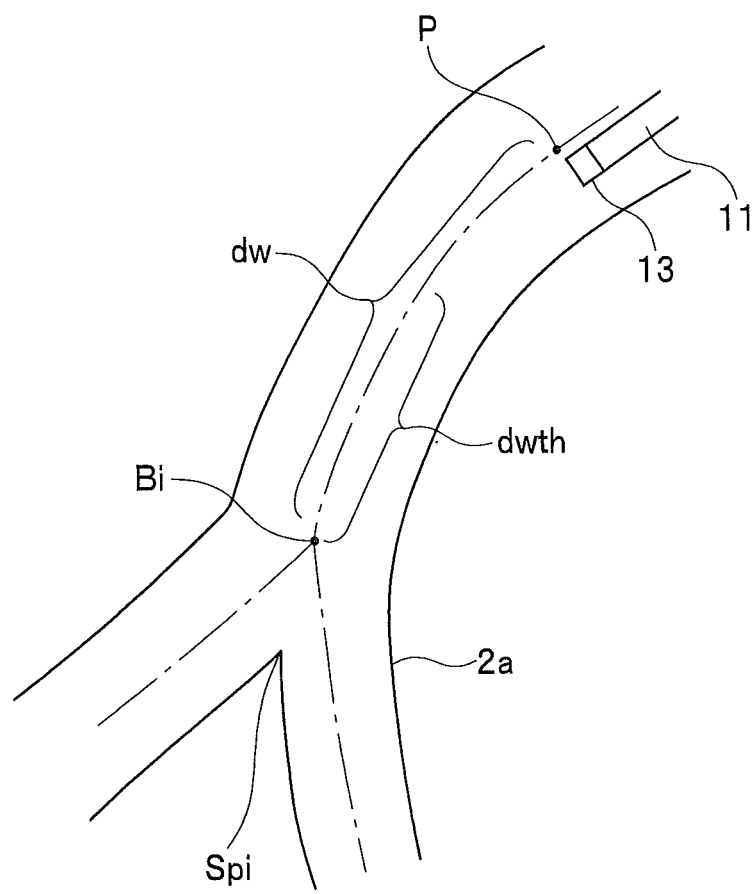
FIG. 4 is a diagram showing a way as a distance from a branch point along a core line.

(f) Moreover, in the examples of FIGS. 2B and 2C, the condition of storage in dependence on whether or not a slant distance between the two points is within the fixed value is shown, but as the condition of storing the candidate information, it may be set whether or not a distance dw on the core line 35 (a distance measured along the core line 35) from a point P on the core line 35 which is the nearest to the position of the distal end of the insertion portion 11 to the branch point Bi is within a fixed value dwth, as shown in FIG. 4.

With the above modifications, the candidate information can be stored and presented appropriately even in a case of insertion into a bent luminal region.

Figure 5A:
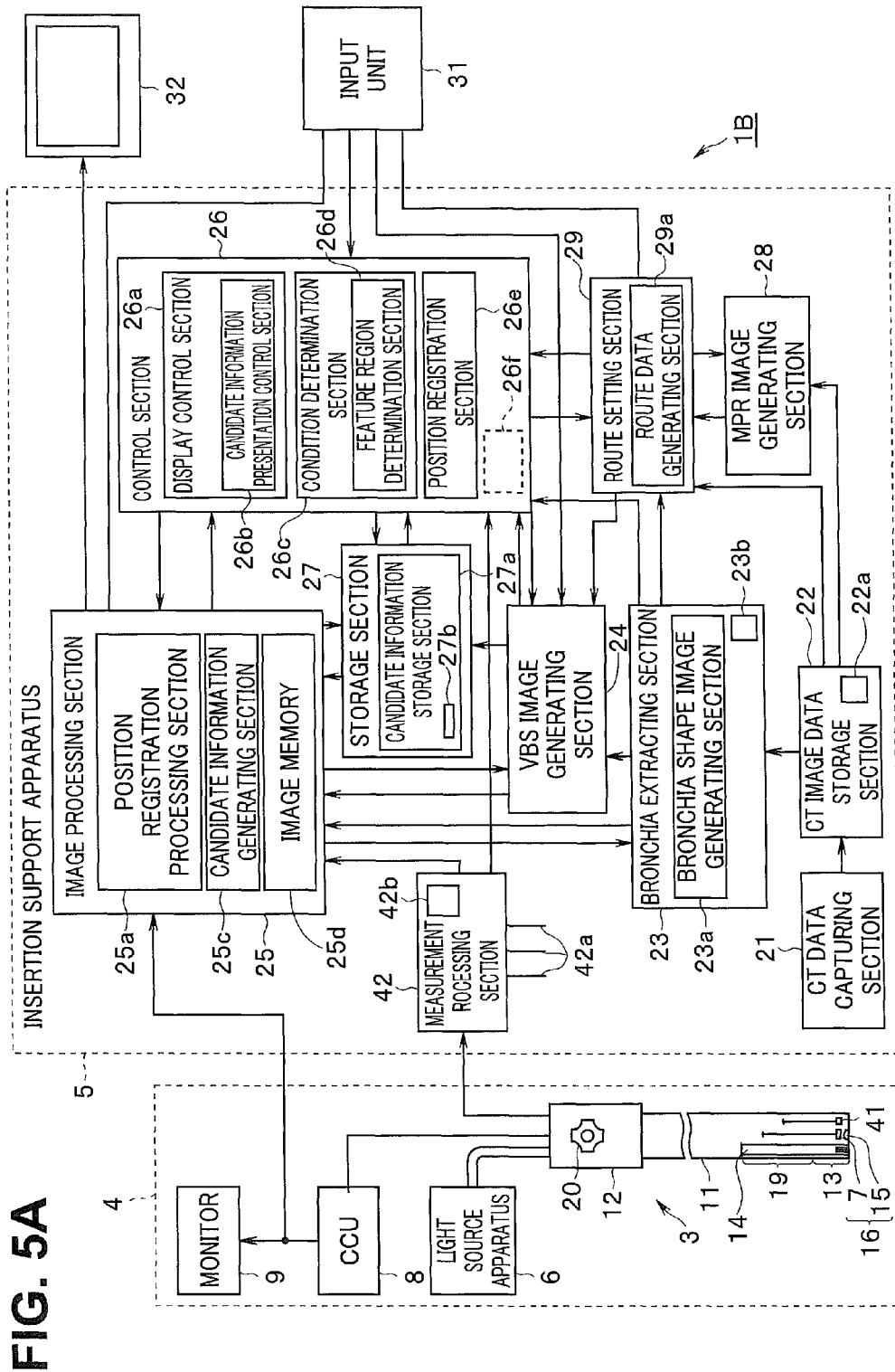
FIG. 5A is a diagram showing an entire configuration of an endoscope system according to a modified example of the first embodiment.

FIG. 5A shows a configuration of an endoscope system 1B in a modified example of the first embodiment. The endoscope system 1B shown in FIG. 5A is further provided with a position sensor 41 for detecting the position of the image pickup unit 16 or the distal end of the insertion portion 11 in the vicinity of the image pickup unit 16 in the distal end portion 13 of the insertion portion 11 in the endoscope system 1 of FIG. 1.

Further, at a predetermined position in the insertion support apparatus 5 outside of the endoscope 3 and the subject, a measuring processing apparatus or measurement processing section 42 that performs processing of measuring (detecting) a three-dimensional position (which is also referred to simply as a position) of the position sensor 41. A detection signal by the position sensor 41 is inputted to the measurement processing section 42.

The measurement processing section 42 has a function of a position estimation section 42b as position detection means that detects or estimates a three-dimensional position of the image pickup unit 16, which constitutes the image pickup means, or a three-dimensional position of the distal end of the insertion portion 11 to be inserted into the bronchia 2 as the specified luminal organ. It is noted that in FIG. 5A of the present modified example, there is not provided the position estimation section 25b in the image processing section 25, which is provided in FIG. 1.

As means or a method for the position detection (position estimation), means or a method using magnetism can be utilized for example. An alternating magnetic field generated by a plurality of antennas 42a connected to the measurement processing section 42 is sensed by the position sensor 41 constituted by a coil, and an amplitude and a phase of a signal detected by the position sensor 41 are detected by the measurement processing section 42 (including an amplitude detecting circuit and a phase detecting circuit), thereby a distance from an antenna 42a to the position sensor 41 is measured. The measurement processing section 42 specifies a three-dimensional position of the position sensor 41 by providing the plurality of, three or more, antennas 42a at known different positions.

Besides, it may be configured such that an alternating signal is applied to the coil constituting the position sensor 41 to generate an alternating magnetic field in the periphery thereof and the alternating magnetic field is sensed by the antennas 42a so that the location of the position sensor 17 is detected. Although the magnetic position detecting apparatus using the coil has been described as an example, the configurations of the position sensor 41 and the measurement processing section 42 are not limited to the above-described case.

For example, it may be configured such that a plurality of coils are arranged for position detection at predetermined intervals along a longitudinal direction of the insertion portion 11 and a shape of the insertion portion 11 is estimated from the positions of the plurality of coils, so that positions of the distal end portion 13, etc. can be detected. The position information of the distal end of the insertion portion 11 detected (estimated) by the measurement processing section 42 is outputted to the control section 26 and the image processing section 25.

In the case of the present modified example, position registration of a position (position information) in a first coordinate system as a CT coordinate system for managing image data of the three-dimensional shape of the bronchia 2, and a position (position information) in a second coordinate system as a sensor coordinate system on the basis of the antennas 42a of the position sensor 41 is performed. For example, the control section 26 has a function of a position registration (and position registration control) section 26e that performs the position registration of the two coordinate systems and the control thereof.

Figure 5B:
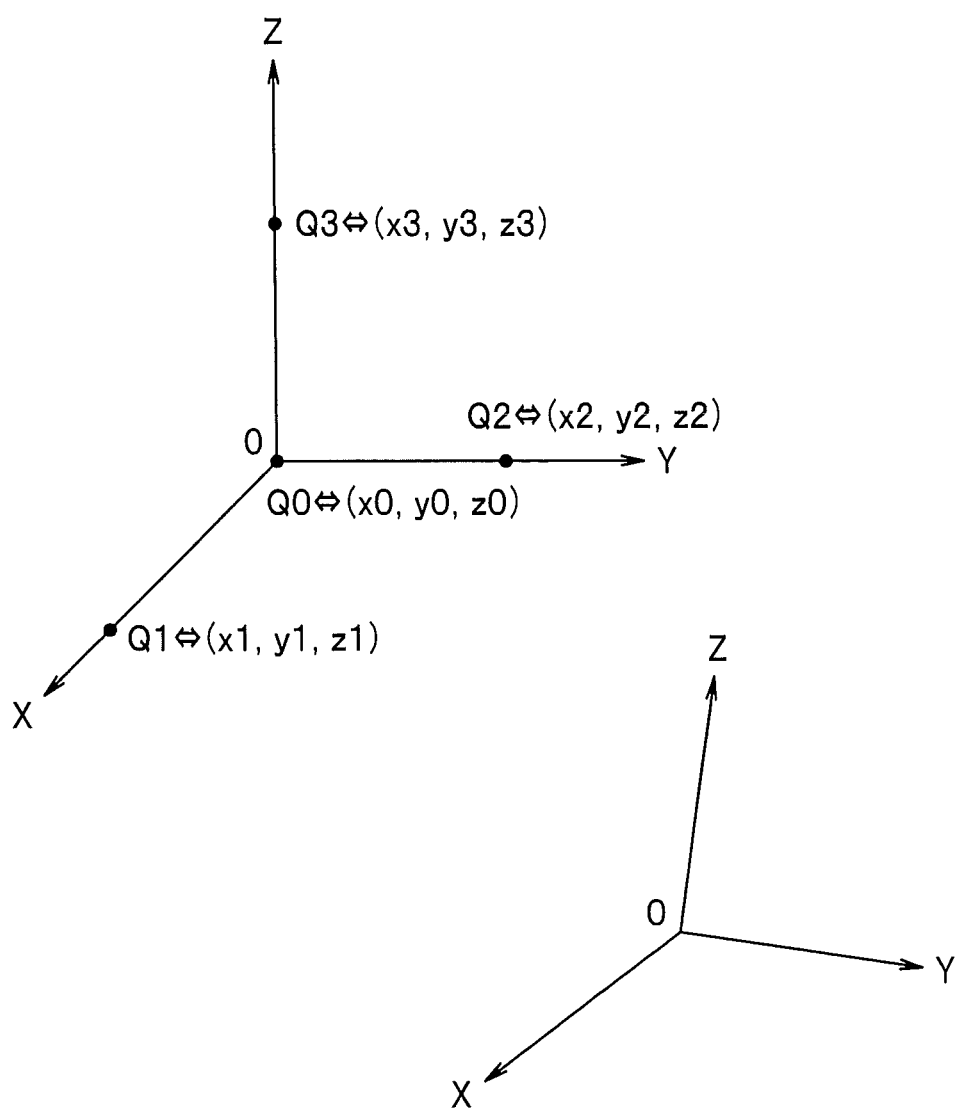
FIG. 5B is an explanatory diagram of registration as correspondence processing between two coordinate systems.

FIG. 5B shows an explanatory diagram of an operation of the registration. For example, the surgeon sequentially sets the distal end portion 13 (or the position sensor 41) of the endoscope 3 at four points Q0-Q3, for example, in the vicinity of an entrance of the bronchia 2, and performs an instruction or an instruction input to perform position correspondence in the first coordinate system O-XYZ and in the second coordinate system o-xyz from the input unit 31. Thus, the input unit 31 forms an instruction input section or instruction input means that performs an instruction of the position correspondence.

For example, the distal end portion 13 (or the position sensor 41) is sequentially set to the position Q0 (0, 0, 0) of an origin O, the position Q1 (1, 0, 0) on an X coordinate axis, the position Q2 (0, 1, 0) on a Y coordinate axis and the position Q3 (0, 0, 1) on a Z coordinate axis in the first coordinate system o-XYZ, and the surgeon performs instructions for setting the position correspondence. Assuming, in these instructions, that the positions respectively measured by the measurement processing section 42 at the respective positions are (x0, y0, z0), (x1, y1, z1), (x2, y2, z2) and (x3, y3, z3), respectively, the control section 27 performs the position correspondence and performs control to store position correspondence information in the storage section 27.

The storage section 27 stores the position correspondence information on this occasion (specifically, Q0 (0, 0, 0), Q1 (1, 0, 0), Q2 (0, 1, 0) and Q3 (0, 0, 1) in the first coordinate system o-XYZ, and (x0, y0, z0), (x1, y1, z1), (x2, y2, z2) and (x3, y3, z3) in the second coordinate system o-xyz, respectively, being corresponding information).

Further, the position registration section 26e determines conversion information for setting correspondence of an arbitrary position between the two coordinate systems using the position correspondence information stored in the storage section 27. The position registration section 26e makes the conversion information be stored in the storage section 27.

In FIG. 5B, the coordinate positions Q0 (0, 0, 0), Q1 (1, 0, 0), Q2 (0, 1, 0), Q3 (0, 0, 1) and the respectively corresponding coordinate positions (x0, y0, z0), (x1, y1, z1), (x2, y2, z2), (x3, y3, z3) are shown as Q0⇔(x0, y0, z0), Q1⇔(x1, y1, z1), Q2⇔(x2, y2, z2) and Q3⇔(x3, y3, z3) for simplification. It is noted that the position correspondence may be performed (determined) using three points with one point omitted, instead of the four points as shown in FIG. 5B.

Specifically, the surgeon sequentially brings the distal end portion 13 of the endoscope 3 into contact with the positions designated in the first coordinate system. At that time, the VBS image is used as a method of expressing the positions designated in the first coordinate system. That is, the surgeon operates the endoscope so that the VBS image and the endoscopic image appear to be identical with each other.

After completing processing of the position correspondence as described, the surgeon starts performing an endoscopic examination by inserting the insertion portion 11 of the endoscope 2 into the bronchia 2.

In the present modified example, it is determined that the position estimation results in failure when a position displacement of the two coordinate systems is clear such as a case where the position in the CT coordinate system (first coordinate system) which corresponds to the position of the distal end portion of the insertion portion 11 estimated by the position estimation section 42b deviates from the condition of being inside of the lumen of the bronchia 2. The other configurations are the same as those of the first embodiment.

The present modified example operates to perform almost the same processing as that in FIG. 3 which shows the operation of the first embodiment except that the position of the distal end of the insertion portion 11 is estimated using the position sensor 41 and that the position registration when the position registration results in failure is performed by the position registration section 26e of the control section 26.

A second modified example in the first embodiment has the same configuration as the first embodiment, but in this modified example, the position registration processing section 25a of the image processing section 25 performs processing for improving precision of the position registration using the position sensor 41 by the image matching.

That is, in the first embodiment, it is necessary to perform the operation such that the distal end of the endoscope 3 is brought into contact with the designated position, but this operation is difficult and is also a factor of lowering precision of the estimated position. Therefore, the distal end portion 13 of the endoscope 3 is surely brought into contact with the designated position by estimating the position of the distal end portion 13 of the endoscope 3 in the CT coordinate system by the image matching, and changing the designated position based on the estimated position. Thereby, an error of the position displacement can be adjusted to be equal to or lower than a predetermined value.

In this modified example, the position registration processing section 25a of the image processing section 25 has a function of a second position registration section that performs the position registration by the image matching, and the measurement processing section 42 has a function of the position estimation section 42b that detects (or estimates) the position of the distal end of the insertion portion 11.

Further, the position registration processing section 25a has a function of a position registration monitoring processing section that monitors a state of the position registration of the two coordinate systems by the image matching. For example, when the distal end of the insertion portion 11 is inserted into the bronchia 2, the endoscopic image and the position in the second coordinate system by the position estimation section 42b change in accordance with the movement of the distal end of the insertion portion 11.

Further, the VBS image generate by the position information in the CT coordinate system (first coordinate system) and inputted to the image processing section 25 changes in accordance with the change of the position in the second coordinate system. The position registration processing section 25a of the image processing section 25 monitors the two images and when the two images displace from each other by a displacement amount equal to or greater than a preset value, it is determined that the position registration results in failure (or the position registration is necessary).

Further, in this modified example, it is determined that the position registration results in failure (or the position registration is necessary) when the position displacement of the two coordinate systems is clear in such a case where the position in the CT coordinate system (first coordinate system) which corresponds to the position of the distal end of the insertion portion 11 estimated by the position estimation section 42b deviates from the condition of being located within the lumen of the bronchia 2. The other configurations are the same as those of the first embodiment.

The present modified example operates to perform almost the same processing as that in FIG. 3 which shows the operation of the first embodiment except that the position of the distal end of the insertion portion 11 is estimated using the position sensor 41 and that the position registration when the position registration results in failure is performed by the position registration section 26e of the control section 26.

According to the first modified example or the second modified example, it is configured that the candidate information for presentation is stored in the storage section 27 in the middle of performing the operation of inserting the insertion portion 11 by the surgeon, and in the case such as the case where the estimation of the position of the distal end of the insertion portion 11 results in failure, the candidate information for presentation can be presented, and therefore the operation of the insertion can be performed smoothly.

Further, in the first modified example or the second modified example, it is configured that the position estimation of the distal end of the insertion portion 11 is performed using the position sensor 41 after the initial position registration, and when the distance from the position at which the position registration is performed becomes long, an error tends to become large with respect to the state of the initial position registration. In such a case, by the re-registration of position using the position sensor 41 and using the image matching, it is made possible to smoothly perform the operation of insertion into the deeper side from the position at which the re-registration of position is performed.

Besides, in the configuration of FIG. 1 or FIG. 5A, when the above-mentioned predetermined condition is met, the candidate information for presentation is stored in the candidate information storage section 27a of the storage section 27, but it may be configured to provide storage limiting means of the candidate information that limits storage of the candidate information at almost the same candidate position or at the similar candidate position after storing the candidate information.

For example, it may be configured to provide a storage limiting section that inhibits (suppresses) storage of succeeding candidate information after the candidate information is stored when the estimated position of the distal end of the insertion portion 11 is within a preset limit distance from the candidate position, and when the distal end moves by a distance equal to or longer than the preset limit distance, cancels the inhabitation (suppression) of the candidate information to allow the next candidate information when the predetermined condition is newly met. Alternatively, it may be limited to a position at which the distal end first reaches the feature region, a position at which the distal end is last located within the feature region, a position which is the most adjacent to the branch point Bi, or a position at which a forward branch is easy to determine. This selection may be performed by an instruction input to the image processing section 25 or the control section 26 by the surgeon through the keyboard, the mouse or the like constituting the input unit 31.

A configuration of a storage liming section (for the candidate information) 26f provided in the control section 26 is shown by the dotted line in FIG. 1 and FIG. 5A, for example.

With this configuration, the candidate information can be suppressed not to be too large when reading the candidate information stored in the candidate information storage section 27a of the storage section 27 to be presented on the monitor 32, and the surgeon is allowed to perform the operation of the position registration out of the appropriate number of pieces of candidate information which are suitable for the position registration. Therefore, an effect that the surgeon can easily perform the position registration is obtained.

Besides, the limit distance for limiting the storage may be set on the basis of the information of the branch point Bi of the bronchia 2, the spur Sp1, etc. Specifically, the limit distance may be set based on a distance between the branch point Bi and a branch point Bi+1 which exist adjacent to each other along the core line 35 of the bronchia, for example. As a specific example, for example, the limit distance may be set to ½ of the distance between the adjacent branch points.

Further, instead of limiting the condition for storing the candidate information in the candidate information storage section 27a of the storage section 27, it may be configured to store presentation selecting information or presentation limiting information additionally (to the candidate information) so as to selectively extract (i.e. limit) and present only the candidate information suitable for the presentation. For this configuration, the candidate information storage section 27a may store the presentation selecting information or the presentation limiting information so as to include a presentation limiting information storage section 27b that stores the presentation selecting information or the presentation limiting information.

In the case where the above-mentioned predetermined condition is set as a position Pi' at which the condition of being located within the fixed value dth2 from the branch point Bi (the condition of existence within the feature region) is first met, for example, when storing the position Pi' to be the candidate position as the candidate information, (Bi, 1) is additionally stored as the presentation limiting information, for example. Here, (Bi, 1) means (a branch point Bi, a number of the position at which the condition is first met).

Further, when the distal end of the insertion portion 11 is moved to the deeper side, assuming that the next position Pi+1 is reached with an appropriate time interval, when storing the position Pi+1' to be the candidate position as the candidate information, (Bi+1, 2) is additionally stored as the presentation limiting information, for example. In this manner, in the case where a plurality of pieces of the candidate information which meet the condition of existence within the fixed value dth2 from the branch point Bi are stored, when an instruction to present the candidate information for the re-registration of position is issued, it may be limited such that only the candidate information of number "1" at the first position where the condition is first met in the vicinity of the branch point Bi, for example, is presented (displayed). Besides, it can be configured such that the number of pieces of candidate information to be presented on the monitor 32 is changed by changing a condition of the number of pieces of candidate information to be presented, from the input unit 31, for example.

With this configuration also, the candidate information can be suppressed not to be too large when presenting the candidate information on the monitor 32, and the surgeon is allowed to perform the operation of the position registration out of the appropriate number of pieces of candidate information which are suitable for the position registration. Therefore, an effect that the surgeon can easily perform the position registration is obtained.

Further, when generating the bronchia shape image or the VBS image, instead of extracting the three-dimensional image data of the bronchia 2 as the specified luminal organ from the CT image data, the three-dimensional image data may be generated directly from the CT image data by volume rendering. In this case, the bronchia extracting section 23 in FIG. 1 or FIG. 5A is unnecessary and the VBS image processing section 24 generates the two types of images.

Second Embodiment

Next, a second embodiment of the present invention will be described. The present embodiment has the same configurations as those of the endoscope system 1 of FIG. 1 or the endoscope system 1B of FIG. 5A.

The contents of the present embodiment are similar to the contents as described above in (b), and the candidate information is stored when a condition that the distance between the two points meets a first threshold and meets a second threshold. In this embodiment, when the condition that the estimated position of the distal end of the insertion portion 11 is moved to Pi at which the distance from the branch point Bi is within the first threshold dt2 and thereafter further moved to Pi+1 at which the distance from the branch point Bi is equal to or greater than the second threshold dt1 is met, it is determined that the distal end of the insertion portion 11 has reached the branch point Bi and the candidate information when the distance is within the first threshold dt2 is stored.

Figure 6:
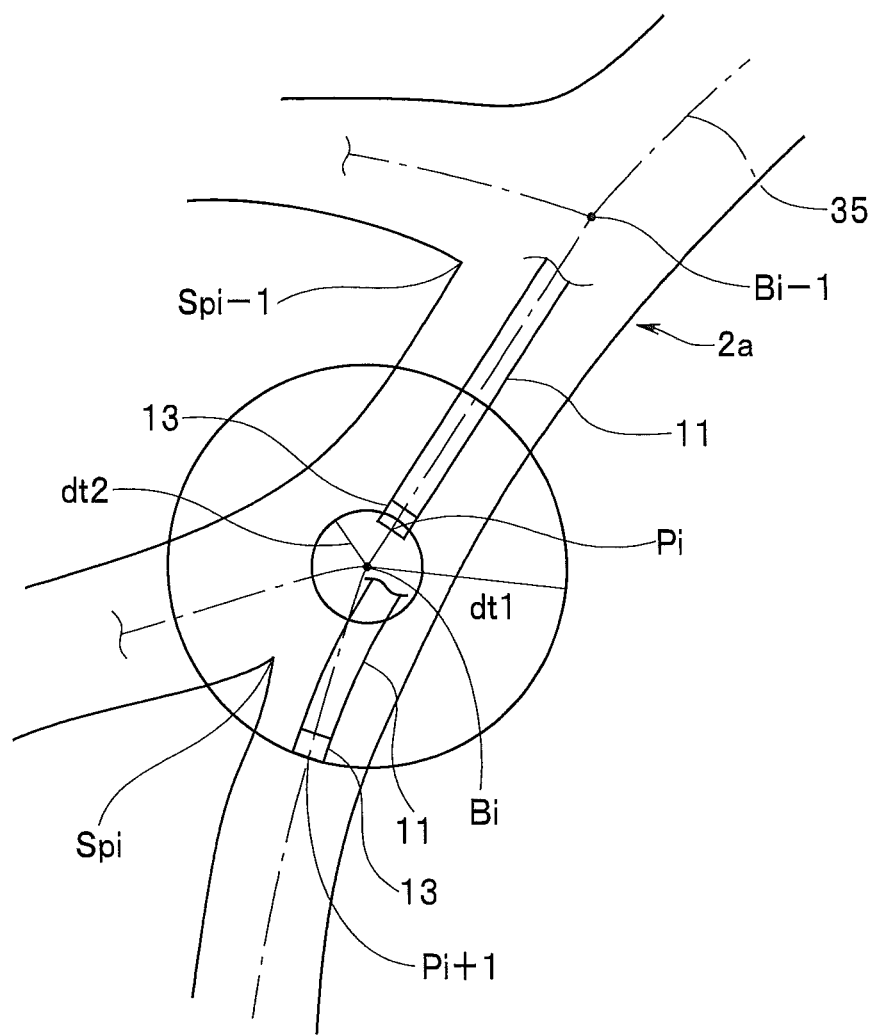
FIG. 6 is an explanatory diagram of an operation in a second embodiment of the present invention.

FIG. 6 shows an explanatory diagram of an operation of storing the candidate information during the operation of insertion in the second embodiment of the present invention. As shown in FIG. 6, the distal end of the insertion portion 11 is inserted into the deeper side with respect to a spur Sp1-1, first determination as to whether or not a distance between an estimated position Pi of the distal end of the insertion portion 11 and a position of the next branch point Bi is within the fixed value dth2 is performed by the feature region determination section 26d of the control section 26.

Further, after the distance between the estimated position Pi of the distal end of the insertion portion 11 and the position of the branch point Bi is determined to be within the first threshold dt2 by the first determination, the feature region determination section 26d further performs second determination as to whether or not the distance between the estimated position Pi of the distal end of the insertion portion 11 and the position of the branch point Bi is less than the second threshold dt1.

When the distance between the estimated position Pi of the distal end of the insertion portion 11 and the position of the branch point Bi becomes a value not less than the second threshold dt1, the candidate information when the distance becomes a value within the first threshold dt2 is stored.

In this case, the first threshold dt1 and the second threshold dt2 are set to be dt1>dt2 as shown in FIG. 6, the candidate information in a state where the distal end of the insertion portion reaches the vicinity of the branch point Bi can be stored as shown in FIG. 6.

According to the present embodiment, it is configured that the candidate information is stored in the storage section 27 in the middle of the operation of inserting the insertion portion 11 by the surgeon, like the first embodiment, and the candidate information for presentation can be presented in a case where the estimation of the position of the distal end of the insertion portion 11 results in failure, or a similar case, and therefore the operation of insertion can be performed smoothly.

Further, according to the present embodiment, the state in which the distal end of the insertion portion 11 reaches a position in the vicinity of the branch point Bi can be precisely detected.

Besides, as the specific example of the present embodiment, it is described that the two thresholds are set for the distance between the position of the distal end of the insertion portion 11 and the branch point Bi, but a distance between the distal end of the insertion portion 11 and the spur Sp1, a distance between a position on the core line 35 which is the nearest to the distal end of the insertion portion 11 and the branch point Bi, etc. may be used.

Third Embodiment

Next, a third embodiment of the present invention will be described. An endoscope system of the present embodiment has the same configuration as the endoscope system 1 of FIG. 1 or the endoscope system 1B of FIG. 5A. In the present embodiment, when the distal end of the insertion portion 11 passes in the vicinity of a branch point and moves to the next bronchiole (branchlet) which is branched from the vicinity of the branch point, the candidate information which has been acquired at the position of the distal end of the insertion portion 11 before the movement to the next bronchiole is stored.

Figure 7:
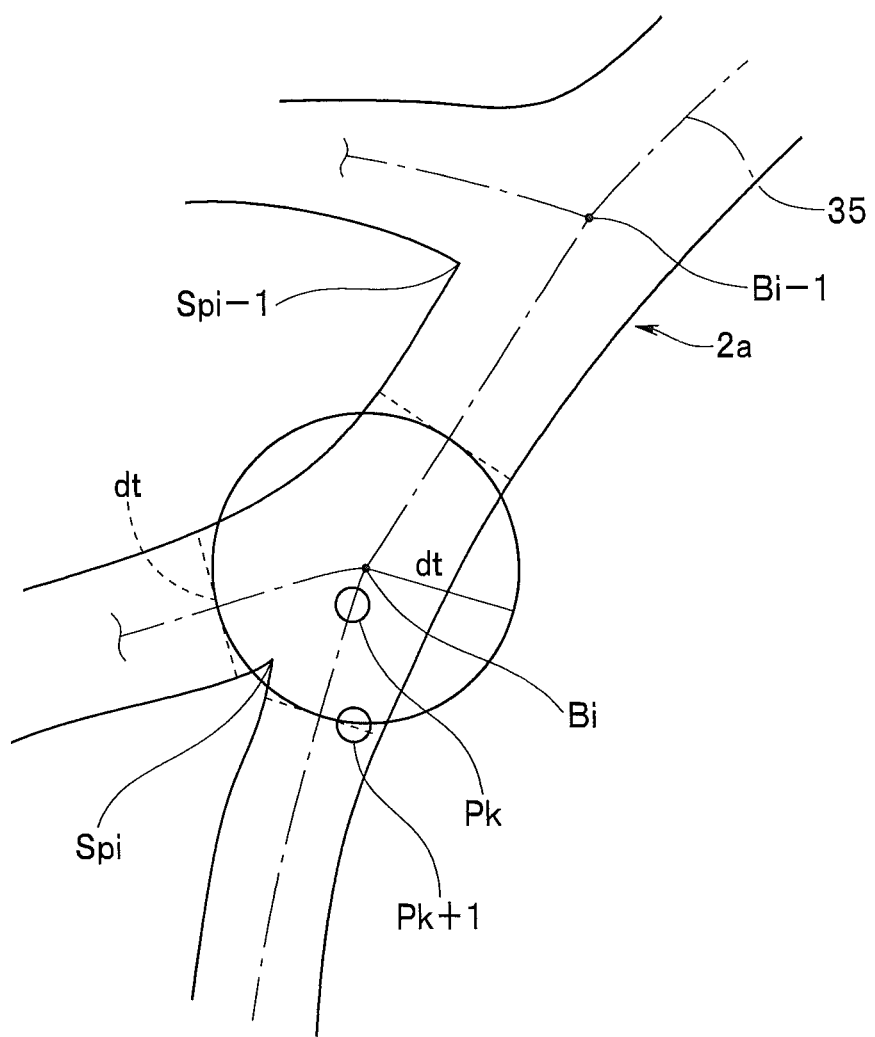
FIG. 7 is an explanatory diagram of an operation in a third embodiment of the present invention.

FIG. 7 shows an explanatory diagram of an operation in the case of the present embodiment. For example, in a case where, after the position of the distal end of the insertion portion 11 is estimated at a position Pk, the distal end of the insertion portion 11 is further moved and reaches a position Pk+1 in one branched bronchiole (branchlet), the candidate information at the position Pk is stored. It is noted that the position of the distal end of the insertion portion 11 is shown by a small circle in FIG. 7 and the subsequent figures.

The case where the distal end reaches (or is moved to) the position Pk+1 in one bronchiole (branchlet) means a case where the core line 35 which is the nearest to the position of the distal end of the insertion portion 11 belongs to the bronchiole, as shown in FIG. 7. In order to determine this state, it may be configured that a region of a circle having a radius dt which is a distance from the branch point B1 as a center is set, and the feature region determination section 26d determines a first state in which the estimated distal end of the insertion portion 11 exists at a location in the region of the circle and then determines a second state in which the distal end of the insertion portion 11 is moved outside the region of the circle. In the example of FIG. 7, the radius dt is set to be a distance between the branch point Bi and the spur Sp1 or a value slightly larger than the distance.

Further, it may be configured that the determination is performed by the endoscopic image. For example, in a case where two dark circular images as images of branched bronchioles are confirmed in the endoscopic image at a location within the circle having the radius dt, and then one dark circular image appears according to the movement of the distal end of the insertion portion 11, the VBS image which has been acquired in a state where an error of the position registration does not occur and corresponds to the position at which the two dark circular images are confirmed may be stored.

Furthermore, as a modified example of the region set to be the circle as shown in FIG. 7, boundaries Bt (shown by the dotted lines in FIG. 7) at which a distance from the branch point Bi on the core line 35 is dt may be set. In the case where the boundaries Bt are set in this manner, substantially the same operational effects are obtained.

Moreover, as a modified example of the present embodiment, when both of distances from the two branch points which the distal end of the insertion portion 11 has passed increase, the VBS image which has been acquired in a state where an error of the position registration does not occur and corresponds to the position immediately before the increase may be stored.

Figure 8:
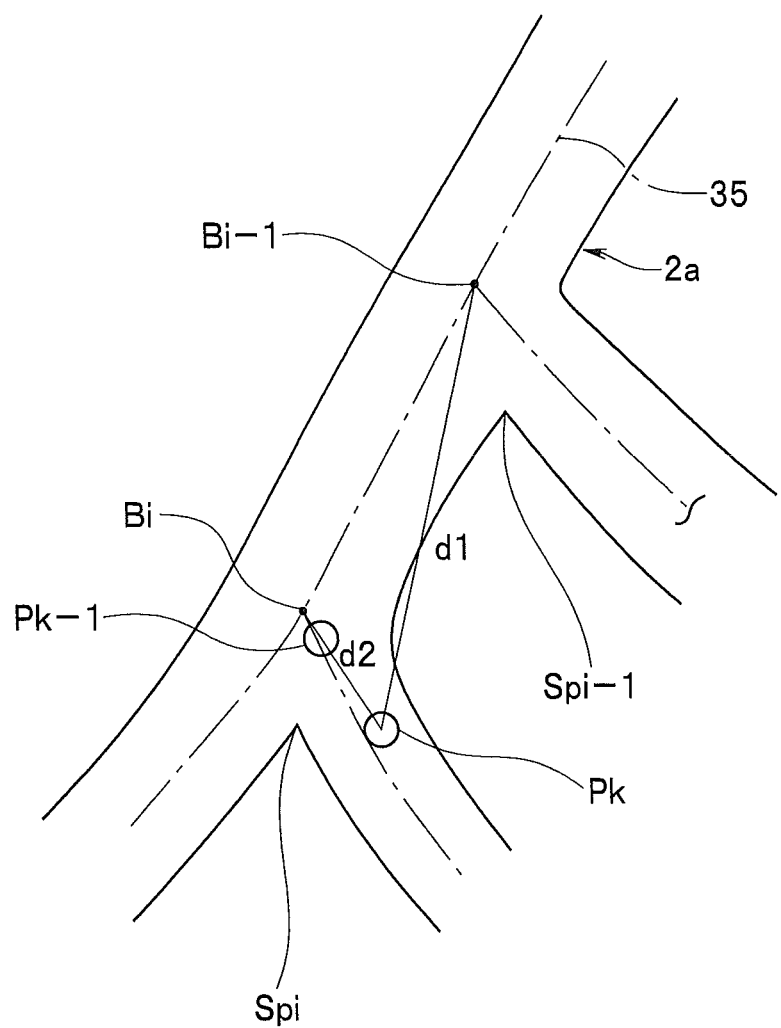
FIG. 8 is an explanatory diagram of an operation in a modified example of the third embodiment of the present invention.

FIG. 8 shows an explanatory diagram of an operation in the case of the present modified example. As shown in FIG. 8, when the estimated position Pk of the insertion portion 11 passes the branch point Bi−1 and the branch point Bi next to the branch point Bi−1, and is inserted into the deeper side (distal side) of the bronchia, the feature region determination section 26d monitors the following condition.

When a condition that a first distance d1 between the branch point Bi−1 and the position Pk and also a second distance d2 between the branch point Bi and the position Pk increase is met, the feature region determination section 26d stores the VBS image which has been acquired in the state where an error of the position registration does not occur and corresponds to a position (e.g. Pk−1) immediately before the position where the above condition is met, as the candidate information.

The present embodiment has substantially the same effects as the second embodiment.

In addition, as shown in FIG. 9, it may be configured such that the candidate information is stored when a distance dg between centers of gravity of the branchlets (bronchioles of the bronchia 2), which serves as a feature value of the branch in the endoscopic image, changes. Besides, upper and lower endoscopic images IK and Ik+1 in FIG. 9 are images acquired when the distal end of the insertion portion 11 is located at positions Pk and Pk+1, respectively, and the image processing section 25 calculates dark portions extracted by binary coded processing or the like as images Ia and Ib of (portions of) the branchlets.

Further, the image processing section 25 calculates centers of gravity Ga and Gb of the images of branchlets Ia and Ib, respectively and estimate the distance dg between the centers of gravity. Then, the image processing section 25 stores, when the distance dg between the centers of gravity Ga and Gb changes by a predetermined value or more, or with a predetermined rate or more in the movement from the position Pk to the position Pk+1, the candidate information at the position Pk, for example. In this configuration, substantially the same effects as those of the third embodiment are obtained. It is noted that a circle outside the images Ia and Ib of the two branchlets shows an inner wall of the lumen of the bronchia 2.

Instead of the case where the distance dg between the centers of gravity Ga and Gb changes as shown in FIG. 9, it may be configured such that the candidate information is stored when a representative radius or a ratio of representative radiuses changes provided that the branchlet is regarded to have an elliptic shape.

Further, it may be configured such that the candidate information is stored when the sum of pixels of the images Ia and Ib changes.

Next, presentation examples of the candidate information in cases where the matching error occurs or the position registration results in failure, or the user issues an instruction to present the candidate information for performing the position registration in the above-described embodiments will be described. In FIG. 2D, one presentation example of the candidate information is shown. However, it may be configured to perform the presentation as follows.

FIG. 10A shows Pc1, Pc2 and Pc3 as the candidate positions stored as the candidate information when the predetermined condition is met in the foregoing embodiments, and V1, V2 and V3 are shown as the corresponding VBS images. Then, when the surgeon gives an instruction to present the candidate information, the candidate positions Pc1, Pc2 and Pc3 are superimposed on the bronchia shape image 2a and the corresponding VBS images V1, V2 and V3 are also displayed to be associated with the candidate positions Pc1, Pc2 and Pc3 (by connecting the candidate position Pc1 (i=1, 2, 3) and the VBS image Vi by a line, or the like). Besides, it may be configured that the endoscope image corresponding to the candidate position Pc1 is displayed simultaneously at a position where the comparison with the VBS image is easily performed.

Further, as shown in FIG. 10A, the target region 36 is displayed to be superimposed on the bronchia shape image 2a and a route R of insertion of the insertion portion 11 of the endoscope 3 is displayed to be superimposed on the bronchia shape image 2a. Further, a locus of the distal end 13 of the endoscope 3, which is not shown, may be displayed.

By presenting the candidate information in the above manner, the user is allowed to easily perform the re-registration of position efficiently in a short time and allowed to easily perform the insertion to the target region 36 smoothly. Besides, it may be configured that, when it is determined the distal end of the insertion portion 11 of the endoscope 3 is moved away from the route R (as the route data) by a predetermined distance (such as a degree of a radius of the lumen), the candidate information as shown in FIG. 10A is presented.

Figure 10B:
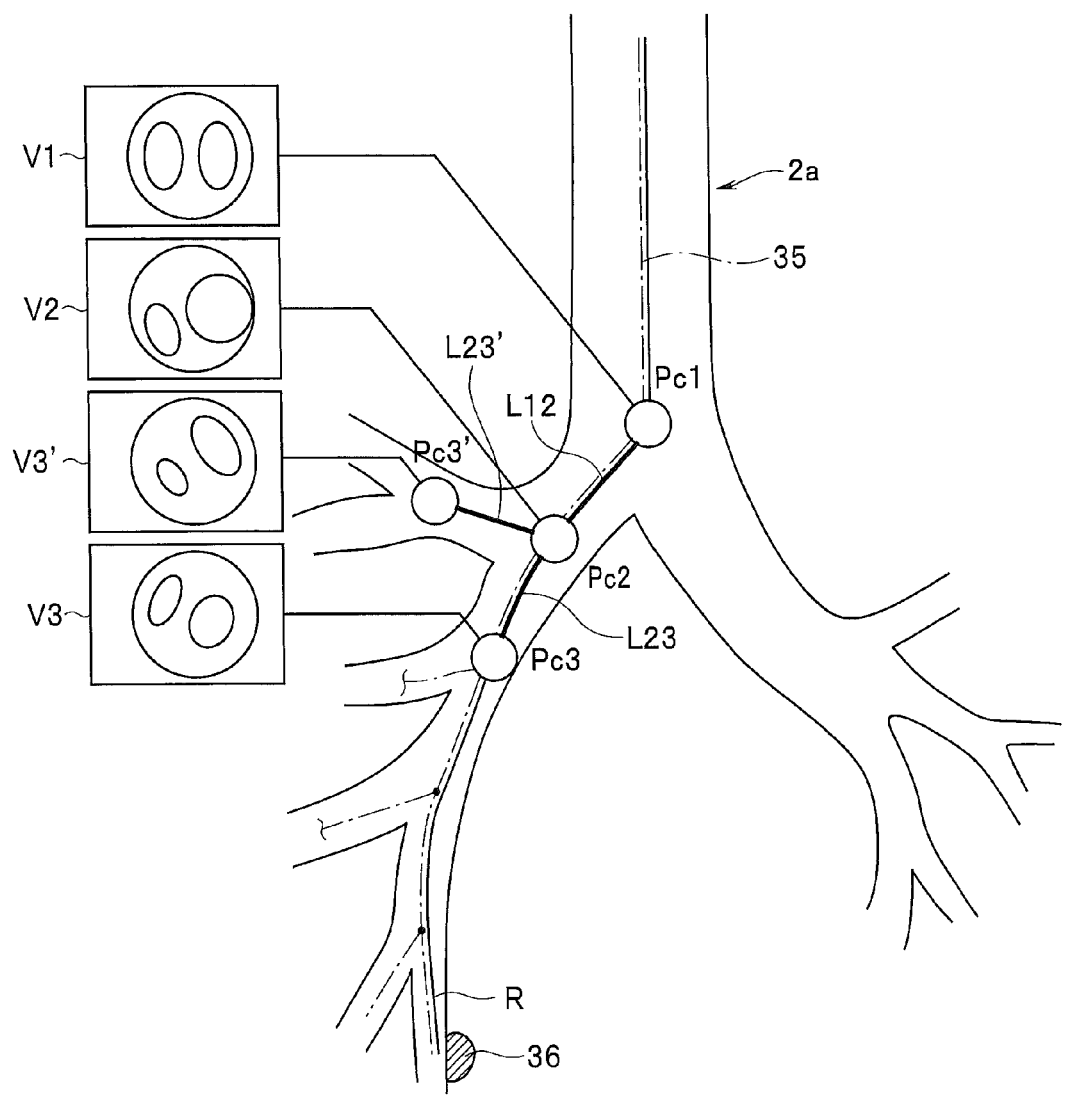
FIG. 10B is a diagram showing a presentation example of candidate information which is different from the presentation example of FIG. 10A.

Further, it may be configured such that the candidate positions Pc1, Pc2, Pc3' and Pc3 are displayed as being connected by lines L12, L23' and L23 along the movement, as shown in FIG. 10B. FIG. 10B shows an example of a case in which, after the candidate information is stored in the order of the candidate positions Pc1, Pc2 and Pc3', the movement is performed to return from the candidate position Pc3' to the candidate position Pc2 and the movement is performed to the candidate position Pc3 at a side of a branchlet different form a branchlet at a side of the candidate position Pc3'. The movement has been performed as describe above, and therefore the lines L12, L23' and L23 are displayed (presented).

It is noted that the VBS image corresponding to the candidate position Pc3' is shown as V3'. The other configurations are the same as described in FIG. 10A and the same effects are obtained.

Figure 10C:
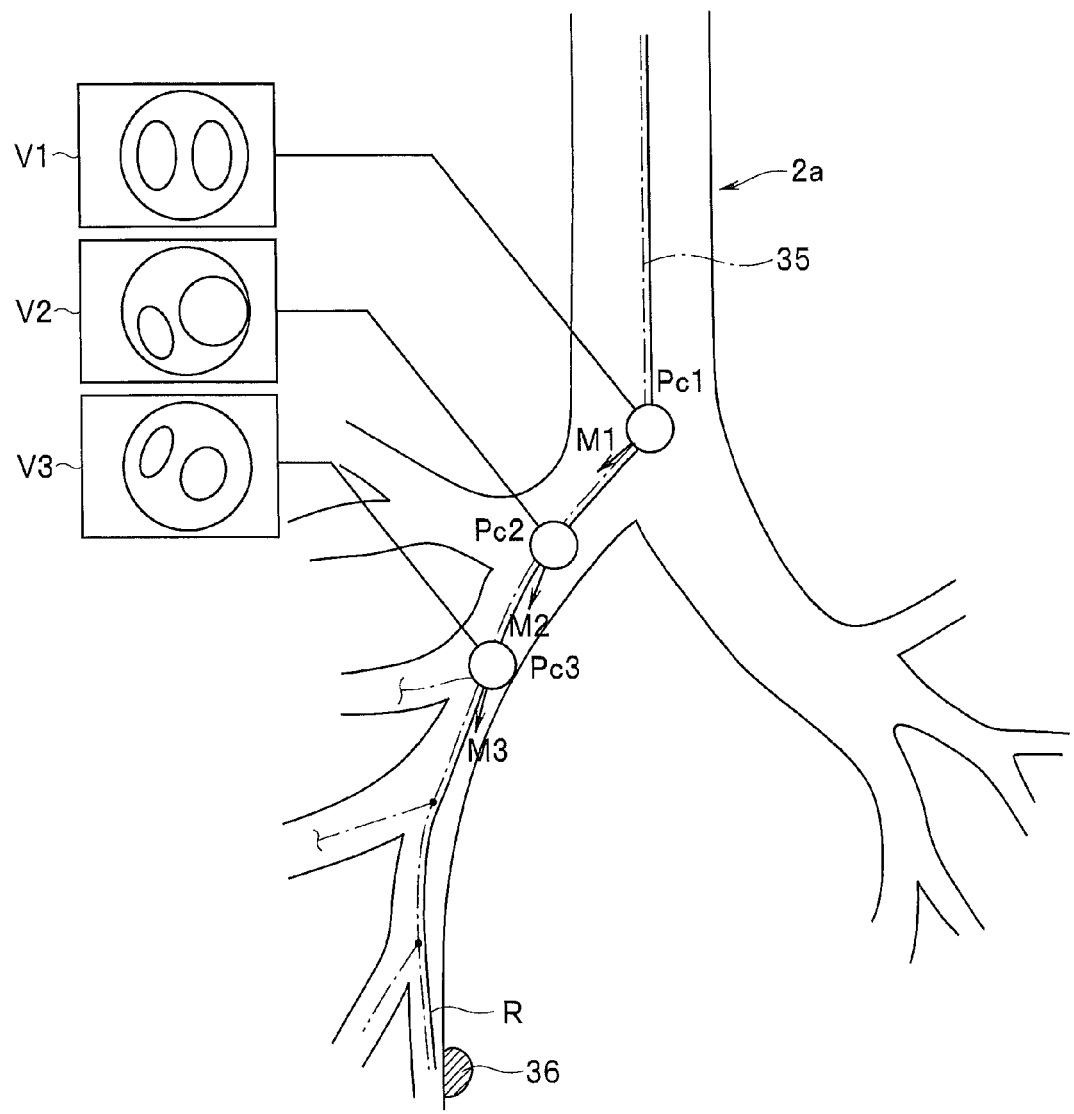
FIG. 10C is a diagram showing a presentation example of candidate information which is different from the presentation example of FIG. 10A.

Further, in FIG. 10C, by acquiring a position of the distal end of the insertion portion 11 when a predetermined time period elapses from a point of time when the candidate information is stored at the candidate position Pc1 of the distal end of the insertion portion of the endoscope 3 in the case of FIG. 10A, for example, a movement direction Mi from the candidate position Pc1 is calculated and stored as the candidate information or supplementary information of the candidate information. Then, as shown in FIG. 10C, the movement direction Mi is also displayed (presented) when presenting the candidate information as described referring to FIG. 10A. The other configurations are the same as described in FIG. 10A and the same effects as those of FIG. 10A are obtained, and the position registration can be performed more easily by referring to the movement direction Mi.

Figure 10D:
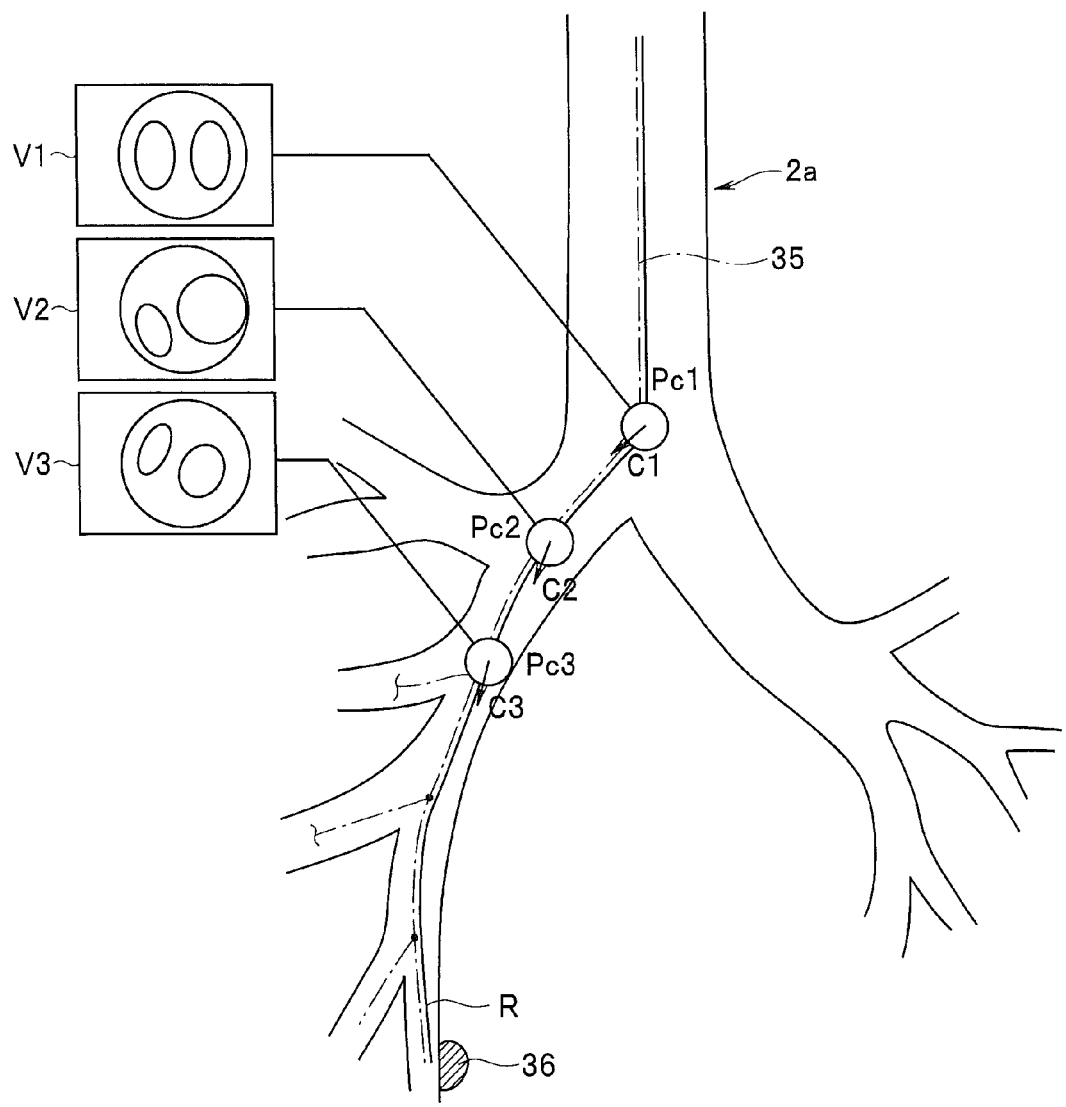
FIG. 10D is a diagram showing a presentation example of candidate information which is different from the presentation example of FIG. 10A.

In FIG. 10D, a direction of a line of sight Ci of the image pickup unit 16 (on the basis of the objective lens 15) is further stored when storing the candidate information at the position Pc1 of the distal end of the insertion portion 11 of the endoscope 3 in the case of FIG. 10A, for example. Then, as shown in FIG. 10D, the direction of the line of sight Ci is also displayed (presented) when presenting the candidate information as described referring to FIG. 10A. The other configurations are the same as described referring to FIG. 10A. The position registration can be performed more easily by the presentation of the direction of the line of sight Ci.

Figure 10E:
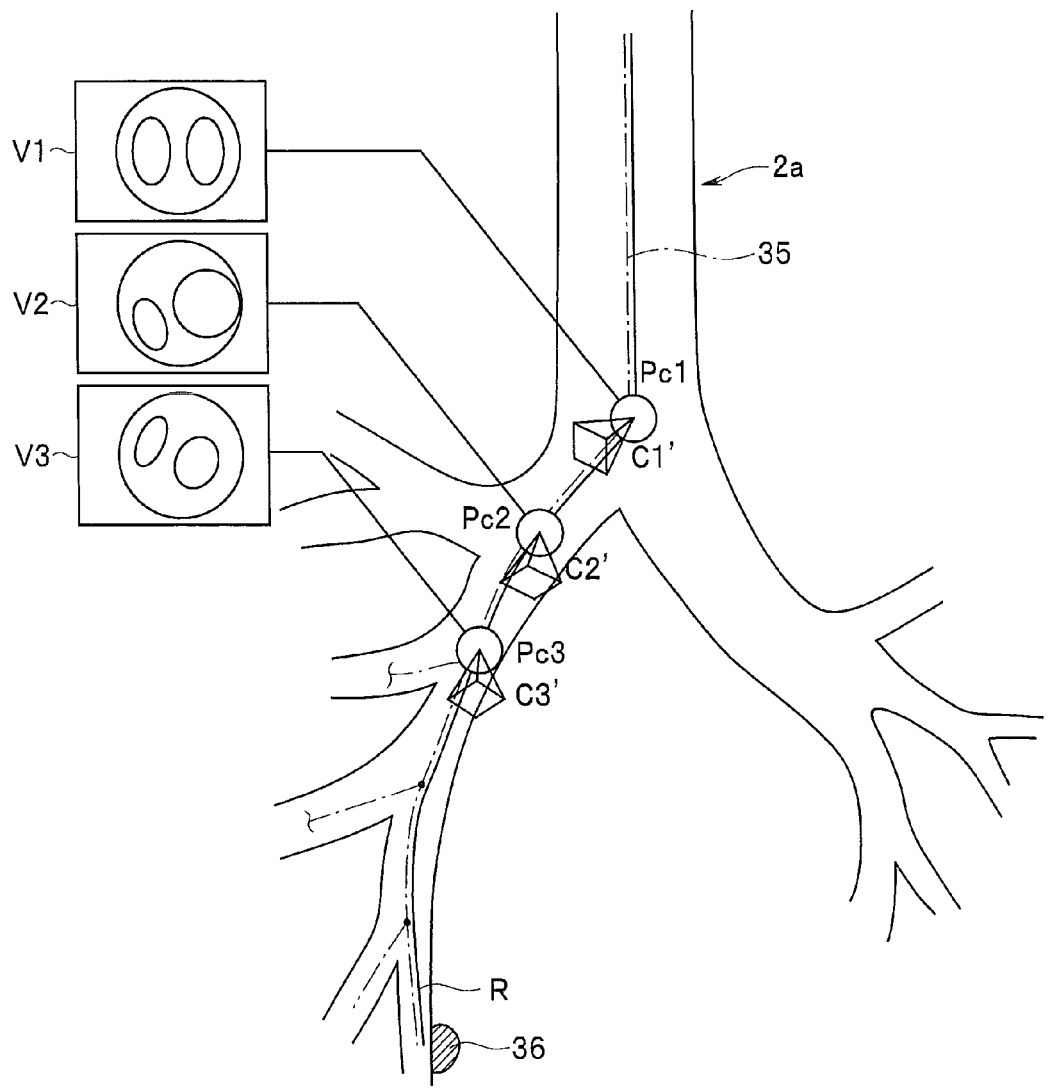
FIG. 10E is a diagram showing a presentation example of candidate information which is different from the presentation example of FIG. 10A.

In FIG. 10D, the example in which the direction of the line of sight Ci can be also presented when presenting the candidate information is described. FIG. 10D shows the case of two-dimensionally displaying the direction of the line of sight Ci. By contrast, as shown in FIG. 10E, it may be configured such that the direction of the line of sight Ci' is displayed using a quadrangular pyramid, for example, so that the direction of the line of sight Ci' is displayed (presented) as a three-dimensional direction to be easily recognized by the user. By the presentation as shown in FIG. 10E, the user can recognize the direction of the line of sight Ci' more easily.

Figure 10F:
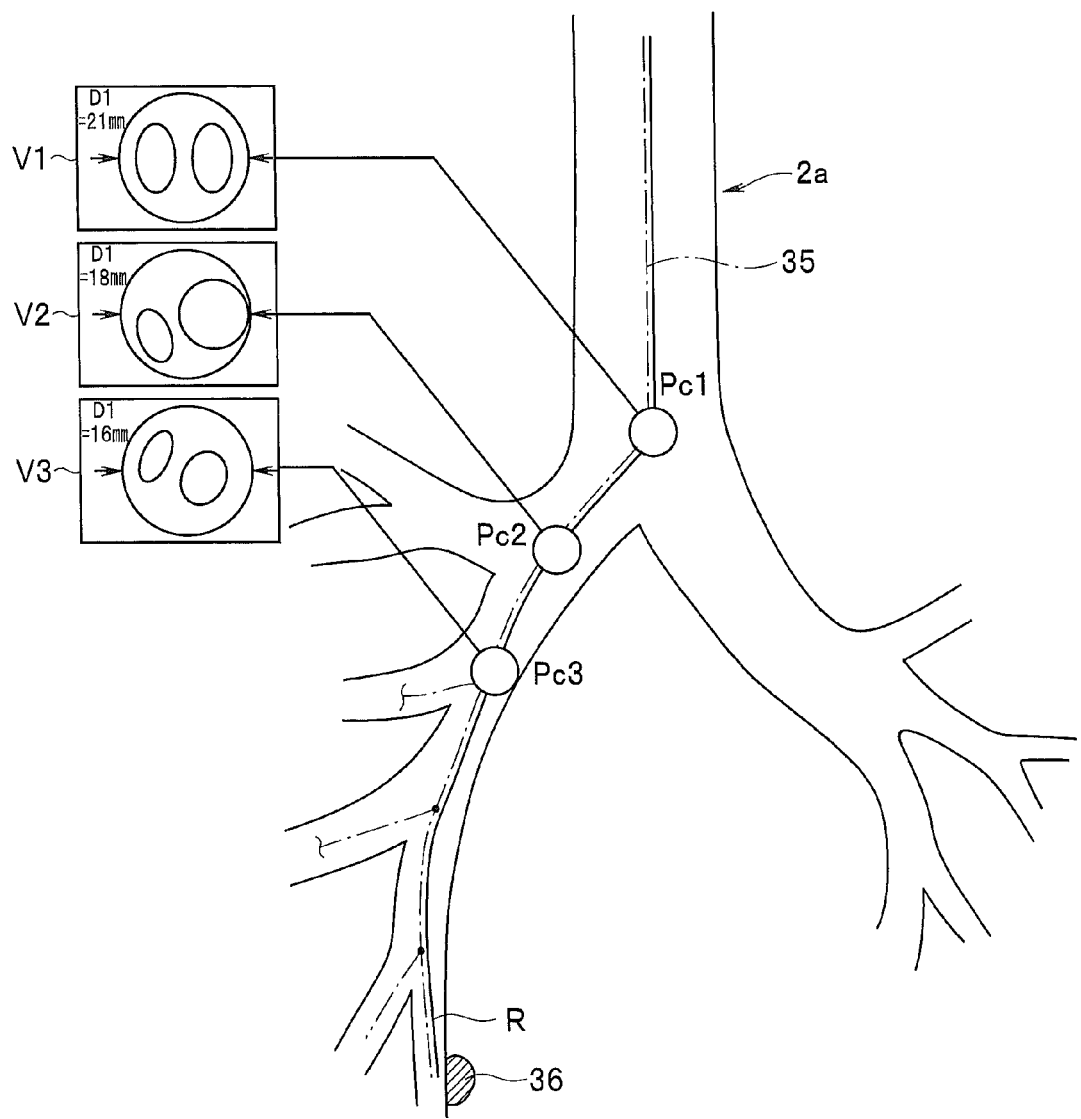
FIG. 10F is a diagram showing a presentation example of candidate information which is different from the presentation example of FIG. 10A.

FIG. 10F shows an example in which information of an inner diameter Di calculated from the three-dimensional shape of the bronchia 2 is further stored as information of a diameter of the lumen of the bronchia 2 when storing the candidate information, and the stored inner diameter Di is also presented when presenting the candidate information. By displaying the information of the inner diameter Di also, as shown in FIG. 10F, the user can grasp the position of the distal end of the insertion portion 11 more easily. The other configurations bring the same effects as those of FIG. 10A.

Figure 10G:
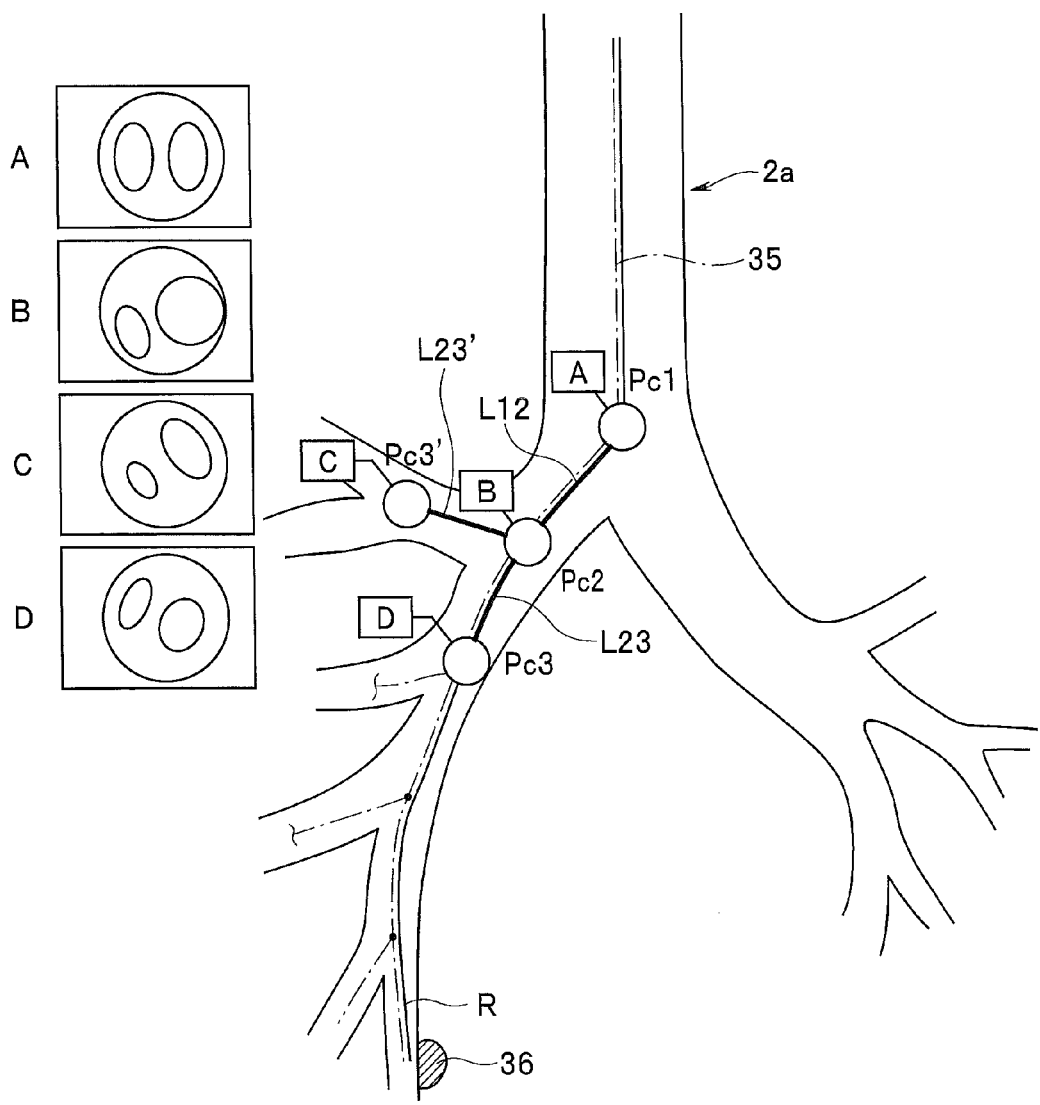
FIG. 10G is a diagram showing a presentation example of candidate information which is different from the presentation example of FIG. 10A.

As shown in FIG. 10G, it may be configured that character information (specifically, A, B, C and D) is added at the four positions and the corresponding VBS images are displayed to be related therewith by the same character information. FIG. 10G shows an example of the case in which, after the candidate information is stored in the order of the candidate positions Pc1, Pc2 and Pc3', the movement is performed to return from the candidate position Pc3' to the candidate position Pc2 and the movement is performed to the candidate position Pc3 at the side of the branchlet different form the branchlet at the side of the candidate position Pc3'. Besides, the VBS images may be arranged on the lower side of the bronchia shape image 2a.

By the presentation as shown in FIG. 10G, the user can confirm the positions in time series and the position of the distal end of the insertion portion 11 can be grasped more easily. Further, as not shown in the figure, the VBS image may be displayed with sequential order or time of the storage of the candidate information added. Further, the character information may be assigned to the positions in the order of Pc3, Pc3', Pc2 and Pc1 as revered in time series or in the order of short distance from the position where the position estimation has succeeded last.

In the above presentation examples, it is described that the candidate information such as the candidate position is displayed to be superimposed on the bronchia shape image 2a, but the position as the candidate position may be displayed on the tomographic image (MPR image) including the bronchia 2, as described below.

FIG. 11 shows an example of display on the monitor 32 which is applicable to the first to third embodiments. The upper-left area in FIG. 11 shows a CT tomographic image in transverse section including patient's bronchia, the upper-right area in FIG. 11 shows a CT tomographic image in longitudinal section perpendicular to the front of the patient, the lower-left area in FIG. 11 shows a CT tomographic image in longitudinal section parallel to the front of the patient, and the lower-right area in FIG. 11 shows a menu screen for setting coordinates by the user.

In FIG. 11, the estimated position (point) of the distal end of the insertion portion 11 (or the image pickup unit 16 provided at the distal end) is displayed by a circle or other shapes of the same color on the tomographic image. In FIG. 11, four positions are displayed in a color (e.g. blue) different from a display color of the tomographic image.

Besides, when presenting the position of the distal end as the candidate position (information) of the candidate information, it may be configured that the position and the VBS image corresponding to the position are displayed to be related with each other by a line as shown in FIGS. 10A-10F, or it may be configured that the character information (specifically A, B, C and D) are added to the four positions and the corresponding VBS images are displayed to be related by the same character information, as shown in FIG. 12.

The cases as described below are examples showing manners of displaying the positions to be superimposed on the tomographic image, and the display of presenting the VBS images corresponding to the positions to be related by the character information or the like is omitted.

Figure 13:
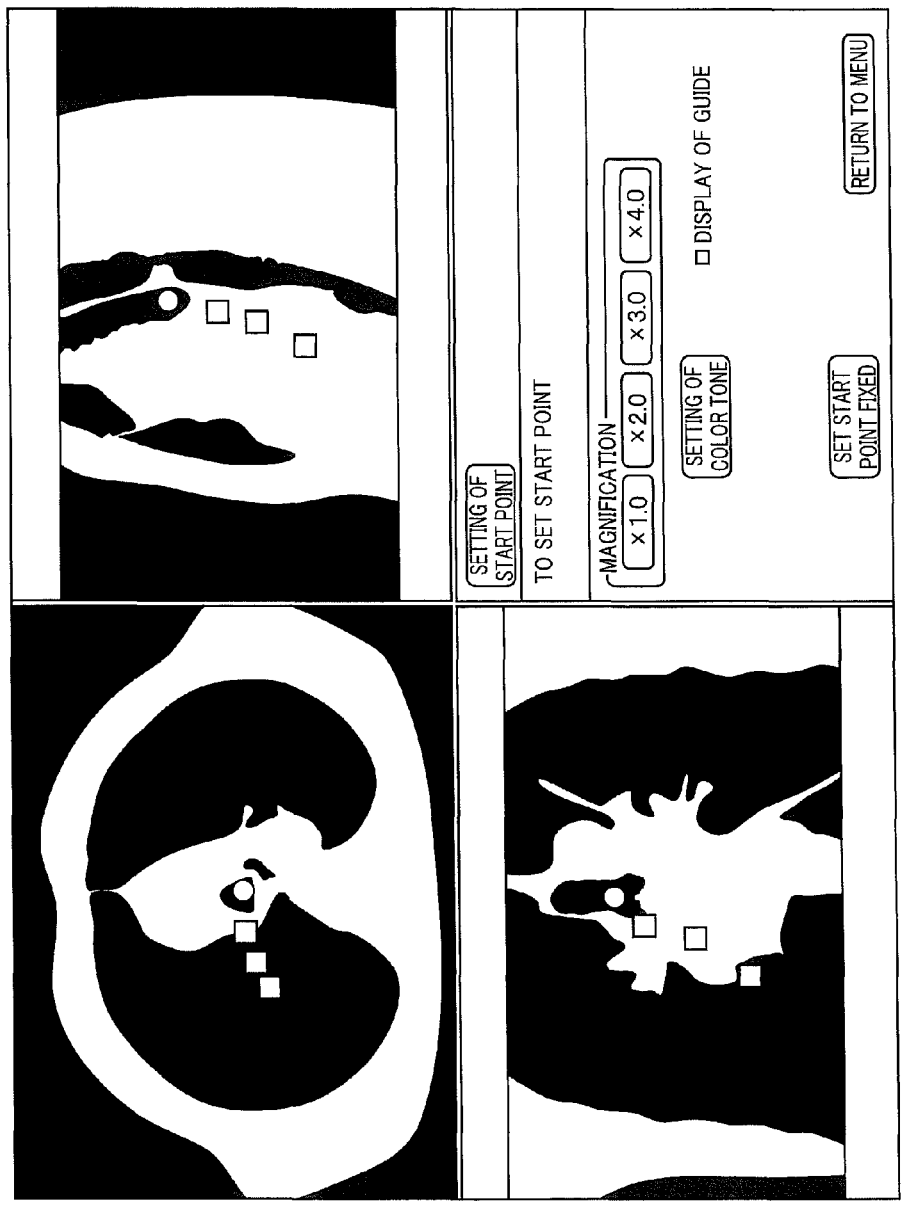
FIG. 13 is a diagram showing a display example corresponding to a modified example of FIG. 11.

In FIG. 11, the estimated positions are displayed in the same color and the same shape for the cases of being present on the section and the other cases, but as shown in FIG. 13, they may be displayed in different shapes for the case of being present on the section and for the case of not being present on the section (for example, the former by circles and the latter by rectangles), or in different colors. Further, only the positions on the section may be displayed.

Figure 14:
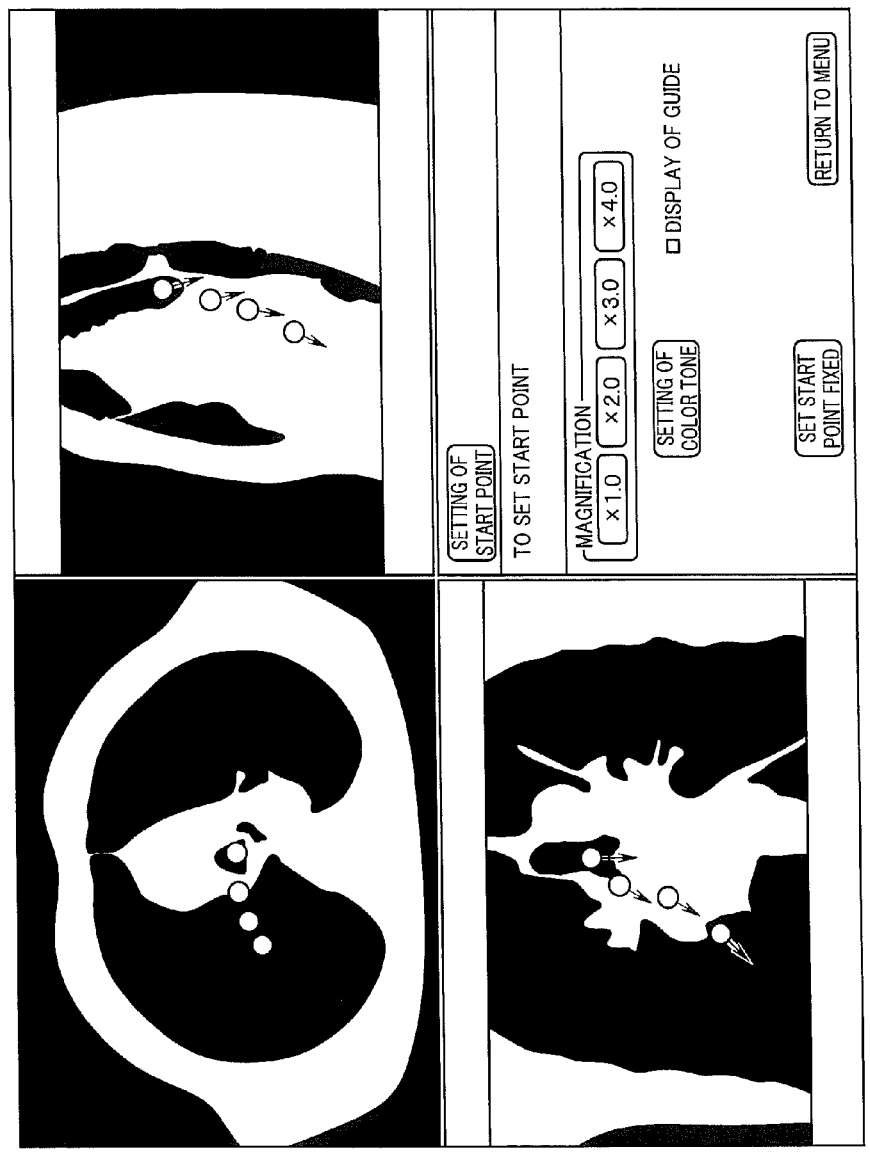
FIG. 14 is a diagram showing a display example of further displaying moving directions in FIG. 11.

For example, in the display of FIG. 11, the information of the movement direction may be also displayed by the arrows as shown in FIG. 14. As described, in the case where the candidate information is stored at the position (of the distal end of the insertion portion 11) when the predetermined condition, such as location within the fixed value from the branch point or the like, is met, the information of the position immediately thereafter is also stored, and an arrow connecting the two points is displayed as the movement direction, as shown in FIG. 13. Besides, instead of indicating the moving direction, the direction of the line of sight of the image pickup unit 16 provided at the distal end of the insertion portion 11 may be displayed.

Figure 15:
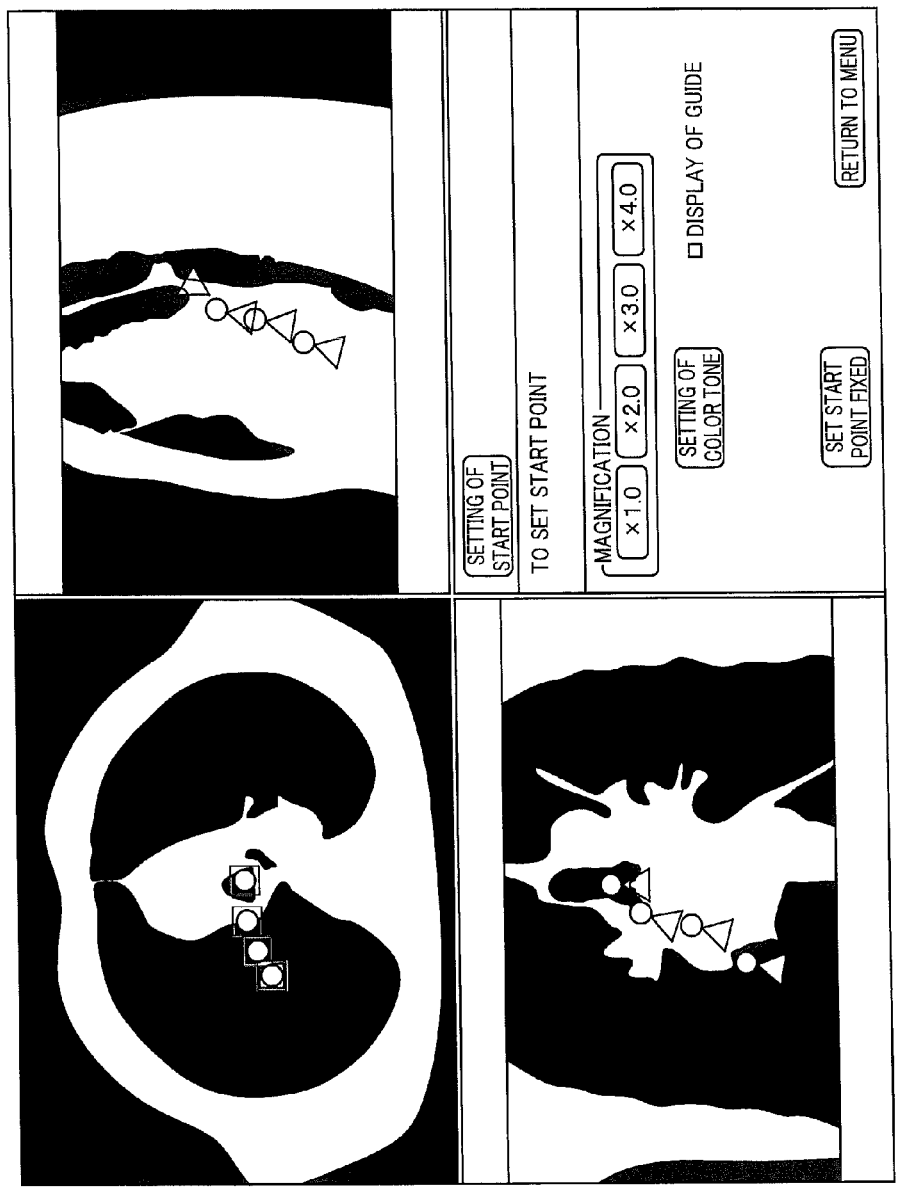
FIG. 15 is a diagram showing a display example of further displaying ranges of fields of view in FIG. 11.

Further, instead of the arrow connecting the two points, the field of view of the image pickup unit 16 or the field of view of the VBS image may be displayed as shown in FIG. 15.

Figure 16:
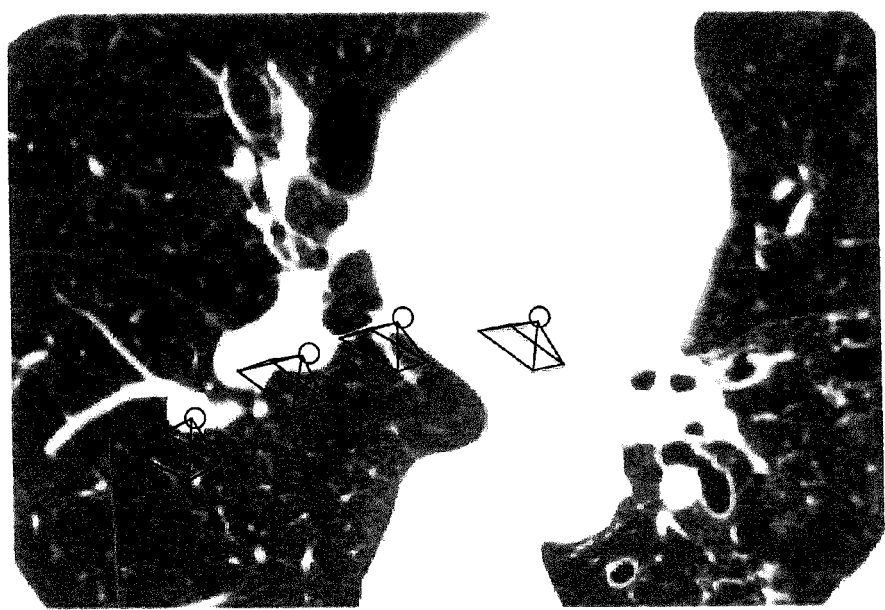
FIG. 16 is a diagram showing a display example of three-dimensionally displaying ranges of fields of view on one tomographic image.

Furthermore, since the display is performed on the MPR image in FIG. 15, the field of view has a shape projected on the section, but the field of view may be displayed three-dimensionally using a quadrangular pyramid in a case of display on one tomographic image, as shown in FIG. 16.

Figure 17:
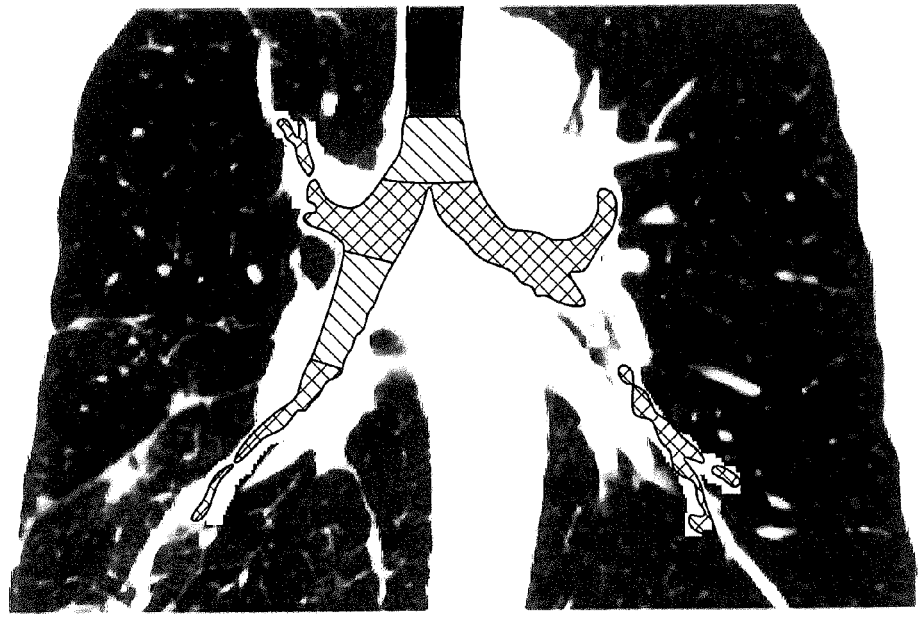
FIG. 17 is a diagram showing an example of displaying stored positions as a region.

Moreover, instead of displaying (presenting) the stored positions by the points, the positions may be displayed (presented) by regions. FIG. 17 shows a presentation example in this case. In FIG. 17, the region indicated by simple hatching is the region already stored (registered) as a candidate region which corresponds to the candidate positions, and the region of cross-hatching shows a region not registered.

By displaying the region already registered and the region not registered to be recognizable in this manner, it is easily recognized whether or not the registration is completed at a branchlet part of the bronchia 2 which the user is interested in. Therefore, the convenience for the user can be improved.

Besides, the region to be displayed (presented) may be a range in which a condition of location within a fixed range from a position where the user or the like instructs the re-registration of position is met, a branchlet in the bronchia 2, or an extracted part in the bronchia 2, to be displayed simultaneously.

Figure 18:
FIG. 18 is a diagram showing an example of displaying a bronchial tree and a tomographic image to be superimposed.

Further, the tomographic image and a bronchial tree may be displayed in combination as shown in FIG. 18 so that the user can easily grasp which part of a lung field the tomographic image (MPR image) in FIG. 11 to FIG. 17 shows.

In this case, the positional relation between the tomographic image and the lung field may be set such that the stored points are placed on the tomographic image, or displaced by an offset value from the points in an arbitrary direction.

Figure 19:
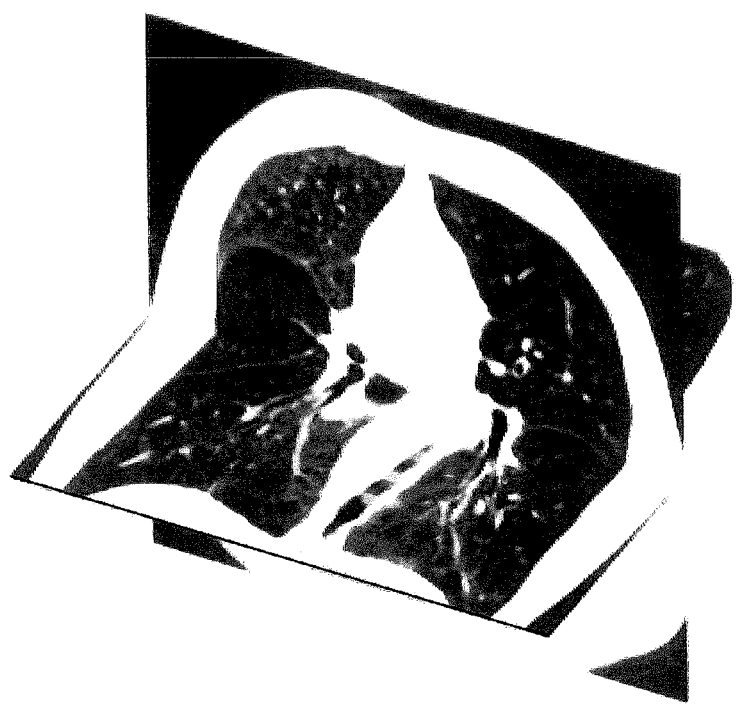
FIG. 19 is a diagram showing an example of performing display using two tomographic images.

Further, FIG. 18 shows an example of displaying one tomographic image, but it may be configured that two or more tomographic images are combined, as shown in FIG. 19.

As the section of the MPR image in FIGS. 11-19 as described above, any of three sections of: a body axis section which is horizontal with respect to a body (an axial section), a sagittal section cut vertically, and a coronal section cut in elevation is used. However, there is a case in which a branch of the bronchial tree is not easily recognized since a shape of the bronchial tree is not taken into account. Therefore, a section including the stored (registered) points of the bronchiole may be set so that the branch is easily recognized, as shown in FIG. 20.

Figure 20:
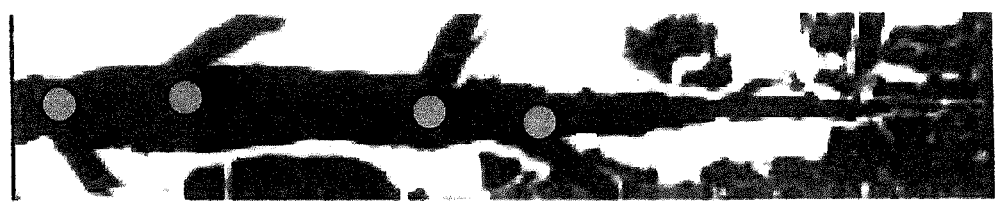
FIG. 20 is a diagram showing an example of displaying stored positions by a cross section including a bronchial tree.
Figure 21A:
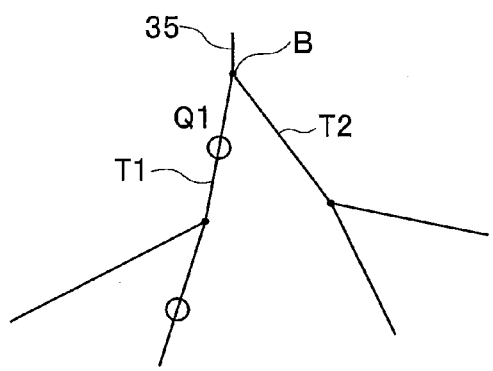
FIGS. 21A to 21D are explanatory diagrams
Figure 21B:
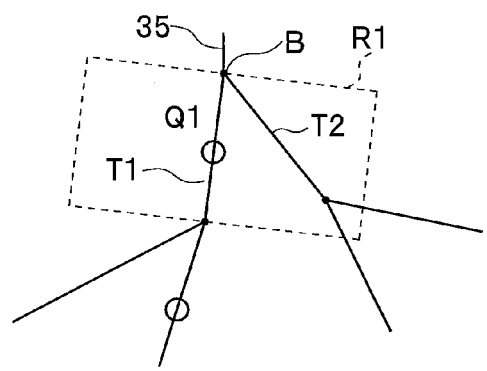
Figure 21C:
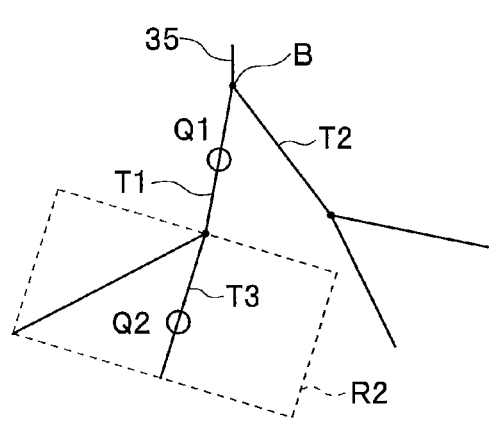
Figure 21D:
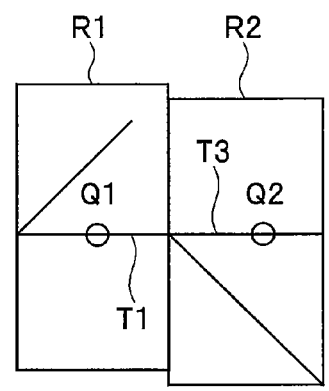

The section shown in FIG. 20 is set by the following set method.

a. As shown in FIG. 21(A), one bronchiole T1 in which a position (point) Q1 stored (registered) as the candidate position in the storage section 27 exists is obtained.

b. As shown in FIG. 21(A), a bronchiole T2 which has the same branch point B as the bronchiole T1 is obtained.

c. An outer product is obtained from direction vectors of the two bronchioles T1 and T2 (for example, from a vector connecting a start point and an end point of the bronchiole, a vector connecting the start point and an intermediate point of the bronchiole on the core line 35, etc.).

d. A plane which includes the branch point B and has the direction vector obtained in c. as a normal line is obtained.

e. As shown in FIG. 21(B), a tomographic image is cut out to include a region R1 on the plane obtained in d. and in accordance with a length of the core line 35 and the direction vector of the bronchiole T1 in which the registered point Q1 exists.

f. The above processing a-e is performed with respect to the bronchioles T1, etc. in which all the registered points Q1, etc. exist. FIG. 21(C) shows a region R2 to be cut out in the same setting manner as shown in FIG. 21(B) with respect to a bronchiole T3 in which a point Q2 on the distal end side in FIG. 21(A) exists.

g. The cut-out regions R1 and R2 are stuck together to generate a stuck tomographic image. In this manner, the section showing the bronchioles including the stored (registered) positions (points) as shown in FIG. 20 is set. By performing the display as shown in FIG. 20, the candidate position is easily grasped from the relation with the bronchioles. Therefore, an effect of easily performing the process of the position registration more smoothly is obtained.

It is noted that embodiments configured by partially combining the foregoing embodiments including the modified examples and so forth belong to the present invention.

What is claimed is:

1. An endoscope system comprising:
  an image storage section that stores image information associated with position information of a luminal organ of a subject;
  a virtual endoscopic image generating section that generates a virtual endoscopic image endoscopically depicted from an arbitrary view point position based on the image information;
  an image pickup section that is provided in an endoscope and picks up an image in the luminal organ of the subject;
  a position registration processing section that compares the virtual endoscopic image generated by the virtual endoscopic image generating section and an endoscopic image generated by image pickup by the image pickup section, and extracts an virtual endoscopic image similar to the endoscopic image;
  a position estimation section that estimates a distal end position of an endoscope insertion portion in the luminal organ of the subject based on position information associated with the virtual endoscopic image extracted by the position registration processing section;
  a feature region determination section that determines whether or not the distal end position of the endoscope insertion portion estimated by the position estimation section exists in a feature region related to a branch in the luminal organ;
  a storage section that stores, when it is determined that the distal end position of the endoscope insertion portion exists in the feature region by the feature region determination section, the distal end position of the endoscope insertion portion estimated by the position estimation section; and
  a candidate information presentation control section that, when the position registration processing section fails to extract a virtual endoscopic image similar to the endoscopic image, presents the virtual endoscopic image corresponding to the distal end position of the endoscope insertion portion which is determined to exist within the feature region by the feature region determination section based on the distal end position of the endoscope insertion portion stored in the storage section, to a display section as candidate information.

2. An endoscope system according to claim 1, further comprising:
  a luminal organ extracting section that extracts a specified luminal organ from the image information and generates a three-dimensional luminal organ image; and
  a route data generating section that generates route data from an insertion start position to a target position in at least the specified luminal organ based on the image information,
  wherein the candidate information presentation control section superimposes the route data on the three-dimensional luminal organ image or a two-dimensional tomographic image which is obtained by cutting the image information in an arbitrary direction, and presents the candidate information upon the route data or in a vicinity of the route data.

3. An endoscope system according to claim 2, comprising a storage limiting section that limits storage of the distal end position of the endoscope insertion portion within a limit distance which is set in accordance with a distance between adjacent branch points in the specified luminal organ when storing the distal end position of the endoscope insertion portion in the storage section.

4. An endoscope system according to claim 1, wherein the feature region determination section determines whether or not the distal end position of the endoscope insertion portion exists in the feature region based on a distance between the distal end position of the endoscope insertion portion and a branch portion at which the lumen branches in the luminal organ.

5. An endoscope system according to claim 1, wherein the candidate information presentation control section presents candidate position information about the distal end position of the endoscope insertion portion corresponding to the virtual endoscopic image in addition to the virtual endoscopic image.

6. An endoscope system according to claim 5, wherein the candidate information presentation control section presents the candidate position information as the candidate information when a position of a distal end of the endoscope insertion portion is moved away from the route data by a predetermined distance.

7. An endoscope system according to claim 1, wherein the candidate information presentation control section presents information of a line of sight of an objective optical system at a distal end of the endoscope insertion portion as the candidate information in addition to the virtual endoscopic image.

8. An endoscope system according to claim 1, wherein the candidate information presentation control section presents information of an inner diameter of the lumen calculated from the endoscopic image as the candidate information in addition to the virtual endoscopic image.

9. An endoscope system according to claim 1, wherein the position estimation section estimates the distal end position of the endoscope insertion portion using a sensor provided at a distal end of the endoscope insertion portion.

10. An endoscope system according to claim 1, wherein the storage section further stores the endoscopic image corresponding to the distal end position of the endoscope insertion portion.

11. An endoscope system according to claim 1, wherein the storage section stores the distal end position of the endoscope insertion portion to include information of numbers stored to be respectively ordered in different feature regions so as to limit the number of pieces of the information which are read from the storage section and presented as the candidate information by the candidate information presentation control section.

12. An endoscope system according to claim 1, wherein the storage section further stores a virtual endoscopic image corresponding to the distal end position of the endoscope insertion portion.

* * * * *